(12) United States Patent
Stamper

(10) Patent No.: US 11,202,622 B2
(45) Date of Patent: Dec. 21, 2021

(54) TISSUE SAMPLE HOLDER WITH ENHANCED FLUID MANAGEMENT

(71) Applicant: Devicor Medical Products, Inc., Cincinnati, OH (US)

(72) Inventor: Melody L. Stamper, Batavia, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 267 days.

(21) Appl. No.: 16/445,389

(22) Filed: Jun. 19, 2019

(65) Prior Publication Data

US 2019/0388071 A1   Dec. 26, 2019

Related U.S. Application Data

(60) Provisional application No. 62/687,465, filed on Jun. 20, 2018.

(51) Int. Cl.
*A61B 10/02* (2006.01)

(52) U.S. Cl.
CPC .. *A61B 10/0275* (2013.01); *A61B 2010/0225* (2013.01)

(58) Field of Classification Search
CPC ........ A61B 10/0275; A61B 2010/0225; A61B 10/0283; A61B 10/0096
See application file for complete search history.

(56) References Cited

U.S. PATENT DOCUMENTS

| | | | |
|---|---|---|---|
| 5,526,822 A | 6/1996 | Burbank et al. | |
| 5,928,164 A | 7/1999 | Burbank et al. | |
| 6,017,316 A | 1/2000 | Ritchart et al. | |
| 6,086,544 A | 4/2000 | Hibner et al. | |
| 6,162,187 A | 12/2000 | Buzzard et al. | |
| 6,432,065 B1 | 8/2002 | Burdorff et al. | |
| 6,626,849 B2 | 9/2003 | Huitema et al. | |
| 6,752,768 B2 | 6/2004 | Burdorff et al. | |
| 7,442,171 B2 | 10/2008 | Stephens et al. | |
| 7,648,466 B2 | 1/2010 | Stephens et al. | |
| 7,837,632 B2 | 11/2010 | Stephens et al. | |
| 7,854,706 B2 | 12/2010 | Hibner | |
| 7,914,464 B2 | 3/2011 | Burdorff et al. | |
| 7,938,786 B2 | 5/2011 | Ritchie et al. | |
| 8,083,687 B2 | 12/2011 | Parihar | |
| 8,118,755 B2 | 2/2012 | Hibner et al. | |
| 8,206,316 B2 | 6/2012 | Hibner et al. | |
| 8,241,226 B2 | 8/2012 | Hibner et al. | |
| 8,251,916 B2 | 8/2012 | Speeg et al. | |

(Continued)

*Primary Examiner* — Rene T Towa

(74) *Attorney, Agent, or Firm* — Frost Brown Todd LLC

(57) ABSTRACT

A biopsy device includes a body, an axial tube, a needle assembly, and a tissue sample holder. The body includes a proximal end. The axial tube extends proximally from the proximal end of the body. The axial tube includes at least one aperture. The needle assembly extends distally from the body and includes a needle and a cutter. The cutter is movable relative to the needle. The tissue sample holder is configured to removably couple to a proximal end of the body such that the axial tube is disposed within the tissue sample holder. At least a portion of the tissue sample holder is rotatable relative to the body such that the tissue sample holder is configured to rotate about the axial tube. The tissue sample holder is in fluid communication with the axial tube through the at least one aperture.

19 Claims, 10 Drawing Sheets

(56) References Cited

U.S. PATENT DOCUMENTS

| | | |
|---|---|---|
| 8,454,531 B2 | 6/2013 | Speeg et al. |
| 8,622,924 B2 | 1/2014 | Speeg et al. |
| 8,702,623 B2 | 4/2014 | Parihar et al. |
| 8,764,680 B2 | 7/2014 | Rhad et al. |
| 8,801,742 B2 | 8/2014 | Rhad et al. |
| 8,858,465 B2 | 10/2014 | Fiebig |
| 8,938,285 B2 | 1/2015 | Fiebig et al. |
| 9,095,326 B2 | 8/2015 | Ritchie et al. |
| 9,326,755 B2 | 5/2016 | Fiebig et al. |
| 9,345,457 B2 | 5/2016 | Speeg et al. |
| 9,486,186 B2 | 11/2016 | Fiebig et al. |
| 9,877,706 B2 | 1/2018 | Speeg et al. |
| 2006/0074345 A1 | 4/2006 | Hibner |
| 2008/0228103 A1* | 9/2008 | Ritchie ............... A61M 1/0052 600/563 |
| 2009/0131821 A1 | 5/2009 | Speeg et al. |
| 2010/0152610 A1 | 6/2010 | Parihar et al. |
| 2010/0160819 A1 | 6/2010 | Parihar et al. |
| 2013/0218047 A1 | 8/2013 | Fiebig et al. |
| 2013/0324882 A1 | 12/2013 | Mescher |
| 2016/0166331 A1* | 6/2016 | Leimbach .......... A61B 10/0275 600/567 |
| 2016/0183928 A1 | 6/2016 | Speeg et al. |
| 2018/0153526 A1 | 6/2018 | Nock et al. |
| 2018/0153529 A1 | 6/2018 | Nock et al. |

\* cited by examiner

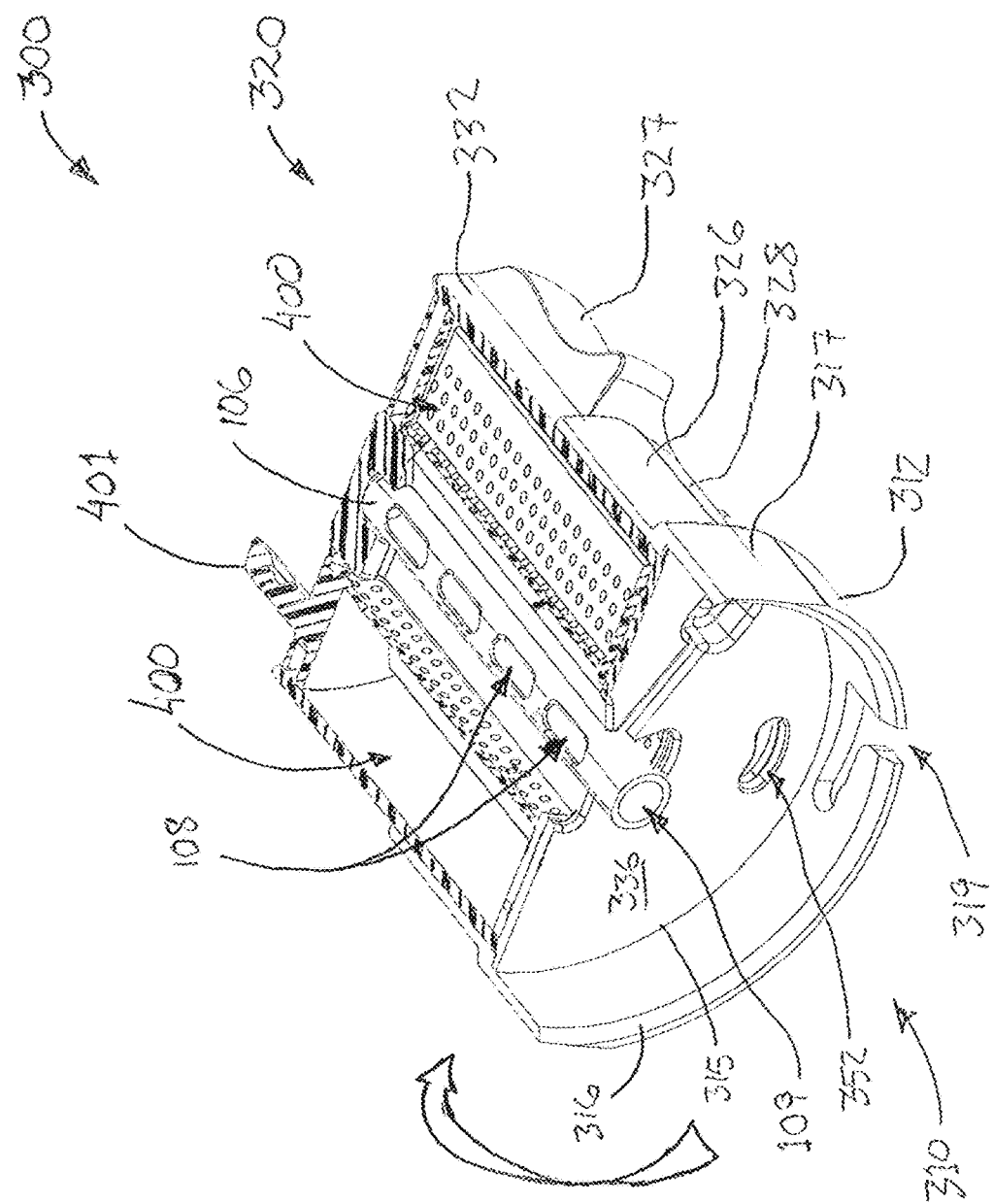

TISSUE SAMPLE HOLDER WITH ENHANCED FLUID MANAGEMENT

PRIORITY

This application claims priority to U.S. Provisional Patent App. No. 62/687,465 entitled "Tissue Sample Holder with Enhanced Fluid Management," filed on Jun. 20, 2018, the disclosure of which is incorporated by reference herein.

BACKGROUND

A biopsy is the removal of a tissue sample from a patient to enable examination of the tissue for signs of cancer or other disorders. Tissue samples may be obtained in a variety of ways using various medical procedures involving a variety of the sample collection devices. For example, biopsies may be open procedures (surgically removing tissue after creating an incision) or percutaneous procedures (e.g. by fine needle aspiration, core needle biopsy, or vacuum assisted biopsy). After the tissue sample is collected, the tissue sample may be analyzed at a lab (e.g. a pathology lab, biomedical lab, etc.) that is set up to perform the appropriate tests (such as histological).

Biopsy samples have been obtained in a variety of ways in various medical procedures including open and percutaneous methods using a variety of devices. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Biopsy devices may be used under ultrasound image guidance, stereotactic (X-ray) guidance, MRI guidance, Positron Emission Mammography ("PEM" guidance), Breast-Specific Gamma Imaging ("BSGI") guidance, or otherwise. Each procedure has its own methodology based on the form of imaging guidance used. The following briefly describes ultrasound image guided biopsy procedures, stereotactic guided biopsy procedures and MIII guided biopsy procedures.

In an ultrasound image guided breast biopsy procedure, the operator may position an ultrasound transducer on the patient's breast and maneuver the transducer while viewing an ultrasound image display screen to locate suspicious tissue in the patient's breast. Once the operator locates the suspicious tissue, the operator may anesthetize the target region of the breast. Once the breast has been anesthetized, the operator may create an initial incision using a scalpel at a location on the exterior of the breast offset from the transducer. A needle of a breast biopsy probe disposed coaxially within an introducer cannula is then inserted into the breast through the initial incision. The operator continues to hold the ultrasound transducer with one hand while maneuvering the biopsy probe with the other hand. While viewing the ultrasound image on the display screen, the operator guides the needle to a position adjacent to the suspicious tissue. A cutter within the needle of the probe is used to remove tissue which is then conveyed either to a manual pick-up location on the breast biopsy device or to a tissue sample chamber. The needle of the breast biopsy device is then removed, leaving the introducer cannula disposed within the breast. The introducer cannula may then be used to introduce a biopsy marker cannula for deploying a biopsy site marker at the biopsy site. Once a marker has been deployed at the biopsy site, the biopsy marker cannula and the introducer cannula are both removed from the breast and the incision is closed using a medically acceptable way to close breaks in the skin.

In a stereotactic image guided breast biopsy procedure, the patient is first positioned relative to x-ray equipment, which includes a breast localization assembly. In some procedures, the patient is oriented in a prone position, with the patient lying face down on a procedure table with at least one breast hanging pendulously through an aperture in the procedure table. The breast is then compressed between a compression paddle and an x-ray receptor of a localization assembly that is positioned under the procedure table. A breast biopsy device is positioned on an automatic guide device in front of the compression paddle and between the breast and an x-ray source. Once positioning of the patient and localization of the breast are complete, a scout image is acquired with the x-ray receptor in a zero-degree angular position (i.e., the x-rays are emitted along an axis normal relative to the x-ray receptor). If the scout image indicates that the patient has been positioned in a desired position, the procedure may proceed with the acquisition of stereotactic image pairs. Stereotactic image pairs are acquired by orienting the x-ray source at various complementary angular positions relative to the x-ray receptor (e.g., +15° and −15°), with at least one x-ray image acquired at each position.

Further in the stereotactic image guided breast biopsy procedure, once a suitable stereotactic image pair is acquired, an operator may identify a target site where biopsy sampling is desired by examining the stereotactic image pair. The target site is marked on each stereotactic image and a precise location of the target site on a Cartesian coordinate system is computed using an image processing module. The computed location of the target site is then communicated to the automatic guide device. The automatic guide device is responsive to this information to position the breast biopsy probe into a position that aligns with the target site. With the breast biopsy device positioned, an operator may then fire a needle of the biopsy probe into the breast of the patient, thereby positioning the needle at the target site. A cutter within the needle of the probe is used to remove tissue, which is then conveyed either to a manual pick-up location on the breast biopsy device or to a tissue sample chamber. After the biopsy tissue is removed, a biopsy marker cannula is inserted into the needle and is used to deploy a biopsy site marker at the biopsy site. Once a marker has been deployed at the biopsy site, the needle is removed from the breast and the incision is closed using a medically acceptable way to close breaks in the skin.

In an MRI guided breast biopsy procedure, after the patient is properly positioned on the table and a targeting device (e.g., a grid and cube combination or a pillar, post and cradle support combination) has been deployed and used, a baseline MRI image is taken to verify the target location. After that, a scalpel is used to incise the skin of the breast. Next, an assembly, formed by an obturator disposed in a sleeve, is inserted through the incision to penetrate the breast tissue under the skin. In some acceptable surgical techniques, the obturator is removed and an imaging rod is inserted into the sleeve in place of the obturator. An imaging rod is defined simply as an appropriately shaped rod that includes a feature that is detectable by an imaging technique being used for the biopsy procedure. The MRI image of the imaging rod is used to locate the site to which the sleeve/ obturator assembly has penetrated. In some other acceptable surgical techniques, the obturator cooperates with the breast tissue to provide a visually observable artifact in an MRI image. With both of these techniques, after the location within the breast where the biopsy is to be taken is confirmed, the obturator or the imaging rod is removed.

Further in the MRI guided breast biopsy procedure, after the obturator or imaging rod has been removed, it is replaced in the sleeve with the needle of a breast biopsy probe. A cutter within the needle of the probe is used to remove tissue, which is then conveyed either to a manual pick up location on the breast biopsy device or to a breast biopsy device sample chamber. After the biopsy tissue is removed, a biopsy marker cannula is inserted into the needle and is used to deploy a biopsy site marker at the biopsy site. The needle is then removed from the sleeve. Optionally, the imaging rod or the obturator is put back into the breast for reimaging of the biopsy site. Then the imaging rod or obturator and the sleeve are removed.

Known biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pat. No. 6,626, 849, entitled "MM Compatible Surgical Biopsy Device," issued Sep. 11, 2003; U.S. Pat. No. 7,837,632, entitled "Biopsy Device Tissue Port Adjustment," issued Nov. 23, 2010; U.S. Pat. No. 7,854,706, entitled "Clutch and Valving System for Tetherless Biopsy Device," issued Dec. 1, 2010; U.S. Pat. No. 7,938,786, entitled "Vacuum Timing Algorithm for Biopsy Device," issued May 10, 2011; U.S. Pat. No. 8,083,687, entitled "Tissue Biopsy Device with Rotatably Linked Thumbwheel and Tissue Sample Holder," issued Dec. 21, 2011; U.S. Pat. No. 8,118,755, entitled "Biopsy Sample Storage," issued Feb. 1, 2012; U.S. Pat. No. 8,241,226, entitled "Biopsy Device with Rotatable Tissue Sample Holder," issued on Aug. 14, 2012; U.S. Pat. No. 8,251,916, entitled "Revolving Tissue Sample Holder for Biopsy Device," issued Aug. 28, 2012; U.S. Pat. No. 8,702, 623, entitled "Biopsy Device with Discrete Tissue Chambers," issued on Apr. 22, 2014; U.S. Pat. No. 8,764,680, entitled "Handheld Biopsy Device with Needle Firing," issued on Jun. 11, 2014; U.S. Pat. No. 8,858,465, entitled "Biopsy Device with Motorized Needle Firing," issued Oct. 14, 2014; U.S. Pat. No. 8,938,285, entitled "Access Chamber and Markers for Biopsy Device," issued Jan. 20, 2015; U.S. Pat. No. 9,095,326, entitled "Biopsy System with Vacuum Control Module," issued Aug. 4, 2015; U.S. Pat. No. 9,095,326, entitled "Biopsy System with Vacuum Control Module," issued Aug. 4, 2015; U.S. Pat. No. 9,326,755, entitled "Biopsy Device Tissue Sample Holder with Bulk Chamber and Pathology Chamber," issued May 3, 2016; U.S. Pat. No. 9,345,457, entitled "Presentation of Biopsy Sample by Biopsy Device," issued May 24, 2016; and U.S. Pat. No. 9,486,186, entitled "Biopsy Device With Slide-In Probe," issued Nov. 8, 2016. The disclosure of each of the above-cited U.S. Patents is incorporated by reference herein.

Additionally known biopsy devices and biopsy system components are disclosed in U.S. Pub. No. 2006/0074345, entitled "Biopsy Apparatus and Method," published Apr. 6, 2006 and now abandoned; U.S. Patent Pub. No. 2009/ 0131821, entitled "Graphical User Interface For Biopsy System Control Module," published May 21, 2009, now abandoned; U.S. Pub. No. 2010/0152610, entitled "Hand Actuated Tetherless Biopsy Device with Pistol Grip," published Jun. 17, 2010, now abandoned; U.S. Pub. No. 2010/ 0160819, entitled "Biopsy Device with Central Thumbwheel," published Jun. 24, 2010, now abandoned; and U.S. Pub. No. 2013/0324882, entitled "Control for Biopsy Device," published Dec. 5, 2013, now abandoned. The disclosure of each of the above-cited U.S. Patent Application Publications is incorporated by reference herein.

U.S. Pat. No. 9,877,706, entitled "Biopsy device" issued Jan. 30, 2018, and U.S. Pub. No. 2016/0183928, entitled "Biopsy Device," published Jun. 30, 2016, both describe some aspect of a biopsy device including a probe, a holster, and a tissue sample holder for collecting tissue samples. The probe includes a needle and a hollow cutter. The tissue sample holder includes a housing having a plurality of chambers that are configured to receive a plurality of strips connected by at least one flexible member. The flexible member is configured to permit the strips to pivot relative to each other such that the strips can shift between a flat configuration and an arcuate configuration. The tissue sample holder is rotatable to successively index each chamber to the cutter lumen such that tissue samples may be collected in the strips. The strips may be removed from the tissue sample holder and placed in a tissue sample holder container for imaging of tissue samples.

In biopsy devices having a multi-chamber tissue sample holder, vacuum can be applied to the tissue sample holder to transport a tissue sample through the probe and into the tissue sample holder. Due to the presence of multiple chambers, it may be desirable to control the distribution of vacuum applied to the tissue sample holder so that the vacuum is directed to a given chamber positioned to receive the tissue sample from the probe. In addition, or in the alternative, it may be desirable to control the distribution of vacuum applied to the given chamber such that vacuum is evenly distributed throughout the given chamber. In some examples, this even distribution of vacuum in the given chamber can be beneficial to avoid unnecessary compression or trauma to the tissue sample.

While several systems and methods have been made and used for obtaining and processing a biopsy sample, it is believed that no one prior to the inventor has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 10B depicts a cross-sectional view of the tissue sample holder of FIG. 11 in a second rotatable position relative to the fluid management tube positioned therein, with the plurality of tissue sample trays received within the plurality of chamber openings, the cross-section taken along line 10-10 of FIG. 5.

Figure 1:
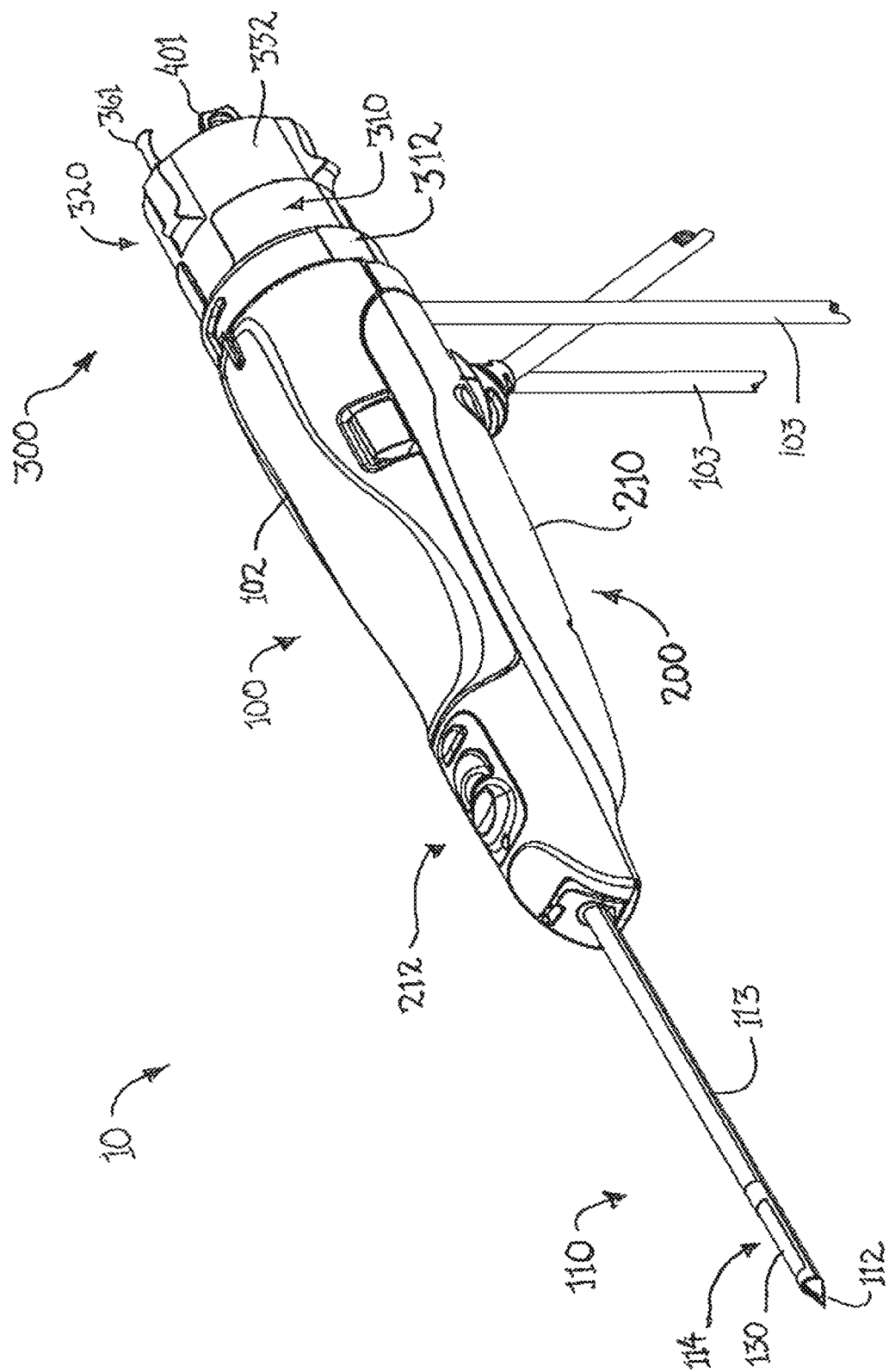
FIG. 1 depicts a perspective view of an exemplary biopsy device with a tissue sample holder assembled thereon.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Exemplary Biopsy Device

FIG. 1 shows an exemplary a biopsy device (10) that may be used in a breast biopsy system including, in some examples, a vacuum control module (not shown). Biopsy device (10) of the present example comprises a probe (100) and a holster (200). A needle (110) extends distally from probe (100) and is inserted into a patient's tissue to obtain tissue samples. These tissue samples are deposited in a tissue sample holder (300) at the proximal end of probe (100), as will also be described in greater detail below.

Holster (200) of the present example is selectively attachable to probe (100) to provide actuation of various components within probe (100). In the present configuration, holster (200) is a reusable component, while probe (100) and tissue sample holder (300) are disposable. It should be understood that the use of the term "holster" herein should not be read as requiring any portion of probe (100) to be inserted into any portion of holster (200). For instance, in the present example, holster (200) includes a set of prongs (not shown) or other retention features that are received by probe (100) to releasably secure probe (100) to holster (200). Probe (100) also includes a set of resilient tabs (not shown) or other suitable release features that may be pressed inwardly to disengage the prongs, such that a user may simultaneously depress both of the tabs then pull probe (100) rearwardly and away from holster (200) to decouple probe (100) from holster (200). Of course, a variety of other types of structures, components, features, etc. (e.g., bayonet mounts, latches, clamps, clips, snap fittings, etc.) may be used to provide removable coupling of probe (100) and holster (200). Furthermore, in some biopsy devices (10), probe (100) and holster (200) may be of unitary or integral construction, such that the two components cannot be separated. By way of example only, in versions where probe (100) and holster (200) are provided as separable components, probe (100) may be provided as a disposable component, while holster (200) may be provided as a reusable component. Still other suitable structural and functional relationships between probe (100) and holster (200) will be apparent to those of ordinary skill in the art in view of the teachings herein.

Some variations of biopsy device (10) may include one or more sensors (not shown), in probe (100) and/or in holster (200), that is/are configured to detect when probe (100) is coupled with holster (200). Such sensors or other features may further be configured to permit only certain types of probes (100) and holsters (200) to be coupled together. In addition, or in the alternative, such sensors may be configured to disable one or more functions of probes (100) and/or holsters (200) until a suitable probe (100) and holster (200) are coupled together. In one merely illustrative example, probe (100) includes a magnet (not shown) that is detected by a Hall Effect sensor (not shown) or some other type of sensor in holster (200) when probe (100) is coupled with holster (200). As yet another merely illustrative example, coupling of probe (100) with holster (200) may be detected using physical contact between conductive surfaces or electrodes, using RFID technology, and/or in numerous other ways as will be apparent to those of ordinary skill in the art in view of the teachings herein. Of course, such sensors and features may be varied or omitted as desired.

Biopsy device (10) of the present example is configured for handheld use, and be used under ultrasonic guidance. Of course, biopsy device (10) may instead be used under stereotactic guidance, MRI guidance, PEM guidance, BSGI guidance, or otherwise. It should also be understood that biopsy device (10) may be sized and configured such that biopsy device (10) may be operated by a single hand of a user. In particular, a user may grasp biopsy device (10), insert needle (110) into a patient's breast, and collect one or a plurality of tissue samples from within the patient's breast, all with just using a single hand. Alternatively, a user may grasp biopsy device (10) with more than one hand and/or with any desired assistance. In still other examples, biopsy device (10) can be configured to be secured to a table or other fixture without handheld operation.

In some settings, whether biopsy device (10) is handheld or mounted to a fixture, the user may capture a plurality of tissue samples with just a single insertion of needle (110) into the patient's breast. Such tissue samples may be deposited in tissue sample holder (300), and later retrieved from tissue sample holder (300) for analysis. While examples described herein often refer to the acquisition of biopsy samples from a patient's breast, it should be understood that biopsy device (10) may be used in a variety of other procedures for a variety of other purposes and in a variety of other parts of a patient's anatomy (e.g., prostate, thyroid, etc.). Various exemplary components, features, configurations, and operabilities of biopsy device (10) will be described in greater detail below; while other suitable components, features, configurations, and operabilities will be apparent to those of ordinary skill in the art in view of the teachings herein.

Holster (200) of the present example includes an outer housing (210) that is configured to at least partially encompass the internal components of holster (200). Although not shown, it should be understood that holster (200) of the present example includes one or more motors and/or other actuators that are configured to drive various components of probe. To communicate power or movement to probe (100), holster (200) can include one or more gears. For instance, in some examples, one or more gears at least partially extend through an opening in outer housing (210). The opening in outer housing (210) can be configured to align with a corresponding opening associated with probe (100) to thereby permit the one or more gears of holster (200) to mesh with one or more corresponding gears of probe (100).

Although not shown, it should be understood that holster (200) may also include various cables that are configured to couple holster (200) to a control module or another control feature. Suitable cables may include electrical cables, rotary drive cables, pneumatic cables, or some combination thereof. Accordingly, it should be understood that in some examples, internal components within holster (200) may be powered by electrical power (electrical cables), rotary power (rotary drive cable), and/or pneumatic power (pneumatic cables). Alternatively, in some examples the cables are omitted entirely and holster (200) can be battery powered with motors and vacuum pumps being entirely contained within holster (200).

As described above, holster (200) of the present example is configured as a reusable portion, while probe (100) is configured as a disposable portion. In some contexts, it may be desirable to maintain sterility of reusable components during a biopsy procedure. Accordingly, in some instances it may be desirable to use holster (200) in connection with certain features to maintain the sterility of holster (200), while also maintaining functionality of holster (200). Merely exemplary features and methods for maintaining the sterility of holster (200) are shown and described in U.S. patent application Ser. No. 15/829,464, entitled "Functional Cover for Biopsy Device," filed on Dec. 1, 2017, the disclosure of which is incorporated by reference herein.

Probe (100) of the present example includes a needle (110) extending distally from probe (100) that is inserted into a patient's tissue to obtain tissue samples. These tissue samples are deposited in a tissue sample holder (300) at the proximal end of probe (100). In some examples, a vacuum control module (not shown) is coupled with probe (100) via a valve assembly (not shown) and tubes (103), which is operable to selectively provide vacuum, saline, atmospheric air, and venting to probe (100). By way of example only, the internal components of the valve assembly of the present example may be configured and arranged as described in U.S. Pat. Pub. No. 2013/0218047, entitled "Biopsy Device Valve Assembly," published Aug. 22, 2013, the disclosure of which is incorporated by reference herein.

As described above with respect to holster (200), probe (100) is selectively couplable to holster (200) so that holster (200) may provide power or otherwise actuate probe (100). In particular, probe (100) includes an outer housing (102) that is received within a probe receiving portion (212) of holster (200). In some examples, holster receiving portion (212) includes an overhang that is configured to permit a portion of probe (100) to nest within holster (200). One or more gears (not shown) are exposed through the opening in outer housing (102) and are operable to drive a cutter actuation mechanism in probe (100). The one or more gears of probe (100) mesh with the one or more gears of holster (200) when probe (100) and holster (200) are coupled together. Accordingly, holster (200) may provide mechanical power or otherwise drive movement of components within probe (100) via gears of probe (100) and holster (200).

Although not shown, in some versions outer housing (102) of probe (100) additionally defines a sample window disposed distally on the exterior of outer housing (102) adjacent to the distal end of outer housing (102). In this instance, it may be desirable for an operator to view samples as they are collected by needle (110). For instance, and as will be described in greater detail below, in the present example tissue sample holder (300) is configured to collect tissue samples in bulk. While this configuration of tissue sample collection may enhance tissue sample capacity, the ability to visualize individual tissue samples may be reduced due to multiple tissue samples being comingled within a common space. Accordingly, a sample window is configured to permit an operator to visualize individual tissue samples as they are collected via needle (110). Although not shown, it should be understood that tissue sample window (140) may be equipped with seals, valves, stoppers, gates, and/or other features to selectively stop the progress of a given tissue sample through probe (100) for viewing via the tissue sample window. In some examples, a tissue sample window may be constructed in accordance with the teachings of U.S. patent application Ser. No. 15/829,483, entitled "Apparatus to Allow Biopsy Sample Visualization During Tissue Removal," filed on Dec. 1, 2017, the disclosure of which is incorporated by reference herein.

Needle (110) of the present example comprises a cannula (113) having a piercing tip (112), and a lateral aperture (114) located proximal to tip (112). Tissue piercing tip (112) is configured to pierce and penetrate tissue, without requiring a high amount of force, and without requiring an opening to be pre-formed in the tissue prior to insertion of tip (112). Alternatively, tip (112) may be blunt (e.g., rounded, flat, etc.) if desired. By way of example only, tip (112) may be configured in accordance with any of the teachings in U.S. Pat. No. 8,801,742, entitled "Needle Assembly and Blade Assembly for Biopsy Device," filed Jun. 1, 2011, the disclosure of which is incorporated by reference herein. As another merely illustrative example, tip (112) may be configured in accordance with at least some of the teachings in U.S. Pat. No. 9,486,186, entitled "Biopsy Device with Slide-In Probe," issued Nov. 8, 2016, the disclosure of which is incorporated by reference herein. Other suitable configurations that may be used for tip (112) will be apparent to those of ordinary skill in the art in view of the teachings herein.

Lateral aperture (114) is sized to receive prolapsed tissue during operation of device (10). A hollow tubular cutter (130) having a sharp distal edge (132) is located within needle (110). Cutter (130) is operable to rotate and translate relative to needle (110) and past lateral aperture (114) to sever a tissue sample from tissue protruding through lateral aperture (114). For instance, cutter (130) may be moved from an extended position to a retracted position, thereby "opening" lateral aperture (114) to allow tissue to protrude there through; then from the retracted position back to the extended position to sever the protruding tissue.

In some examples it may be desirable to rotate needle (110) to orient lateral aperture (114) at a plurality of desired angular positions about the longitudinal axis of needle (110). In the present example, needle (110) can be rotated by a motor disposed in probe (100) or holster (200). In other examples, needle (110) is manually rotatable by a thumbwheel on probe (100) or needle hub directly overmolded onto needle (110). Regardless, it should also be understood that, as with other components described herein, needle (110) may be varied, modified, substituted, or supplemented in a variety of ways; and that needle (110) may have a variety of alternative features, components, configurations, and functionalities. For instance, needle (110) may be constructed in accordance with the teachings of U.S. Pat. No. 9,345,457, issued May 24, 2016, the disclosure of which is incorporated by reference herein, and/or in accordance with the teachings of any other reference cited herein.

As noted above, cutter (130) is operable to simultaneously translate and rotate relative to needle (110) to sever a tissue sample from tissue protruding through lateral aperture (114). Once severed, tissue samples are transported through cutter (130) and into tissue sample holder (300). Although not shown, it should be understood that in the present example probe (100) includes certain cutter actuation components that are configured to translate and rotate cutter (130) relative to needle (110). In some versions, the foregoing cutter actuation components are configured in accordance with at least some of the teachings of U.S. Pat. No. 9,345,457, the disclosure of which is incorporated by reference herein. As yet another merely illustrative example, cutter (130) may be rotated and/or translated using one or more pneumatic motors and/or pneumatic actuators, etc. Still other suitable ways in which cutter (130) may be actuated will be apparent to those of ordinary skill in the art in view of the teachings herein.

II. Exemplary Tissue Sample Holder

Figure 2:
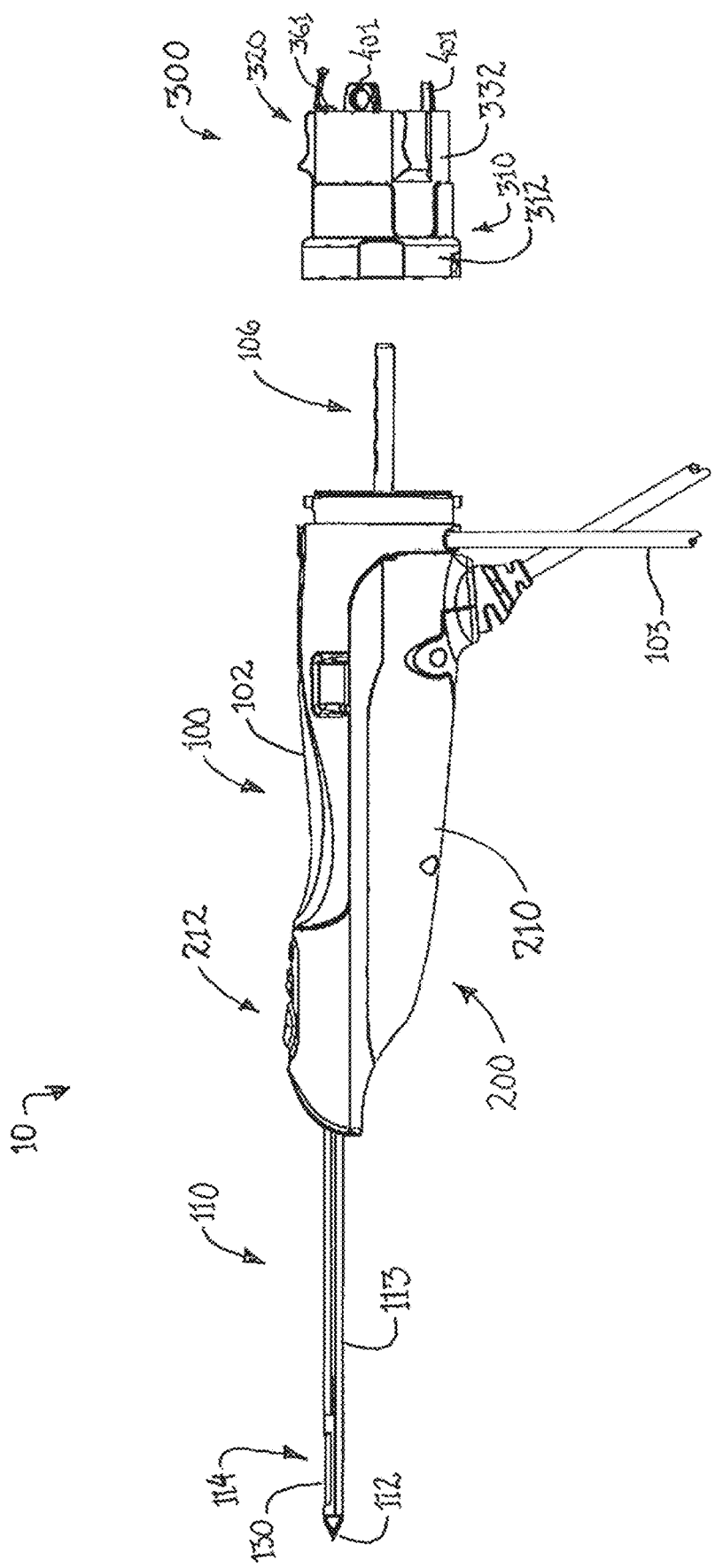
FIG. 2 depicts a side elevational view of the biopsy device of FIG. 1 with the tissue sample holder disassembled, the biopsy device including a fluid management tube.

Tissue sample holder (300) is selectively coupleable to the proximal end of probe (100). As best seen in FIG. 2, probe (100) comprises a fluid management tube (106) that is configured to receive at least a portion of tissue sample holder (300). As will be described in greater detail below, fluid management tube (106) permits tissue sample holder (300) to communicate with probe (100) such that any fluids associated with the tissue samples contained in tissue sample holder (300) may be redirected out of tissue sample holder (300). In some examples, a vacuum may also be communicated through fluid management tube (106) to tissue sample holder (300). In such examples, vacuum is provided to create a fluid circuit through tissue sample holder (300) that pulls tissue samples from cutter (130) and into tissue sample holder (300) and drains tissue sample holder (300) of any residual fluids. As will be described in greater detail below, tissue sample holder (300) is configured to rotate relative to probe (100) about fluid management tube (106) such that fluid management tube (106) serves as the axis of rotation for tissue sample holder (300).

Tissue sample holder (300) of the present example is configured to operate in two discrete sample collection modes—a bulk tissue collection mode and an individual tissue collection mode. As will be understood, by having such a configuration, tissue sample holder (300) provides enhanced flexibility during a biopsy procedure. For instance, an operator may desire to collect tissue sample in a bulk configuration when the operator is removing large quantities of tissue from a patient without a significant interest in analyzing individual samples. However, at various points during the procedure, an operator may desire to have enhanced analysis of an individual tissue sample (e.g., to determine whether tissue sample acquisition is being performed at the margins of a lesion). Thus, it may be desirable to switch from the bulk tissue collection mode to the individual tissue collection mode to conduct further analysis of an individual tissue sample.

Figure 3A:
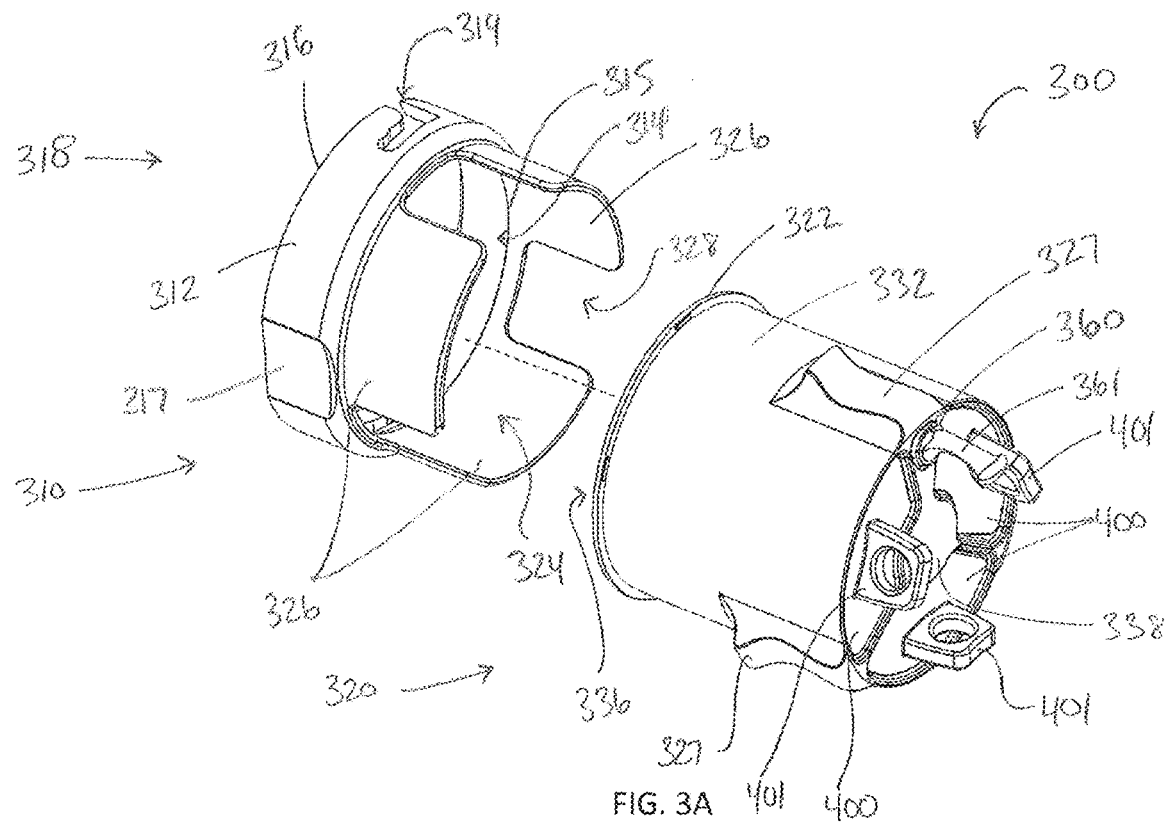
FIG. 3A depicts a perspective view of the tissue sample holder of FIG. 1 including an outer cup and a rotatable member.
Figure 3B:
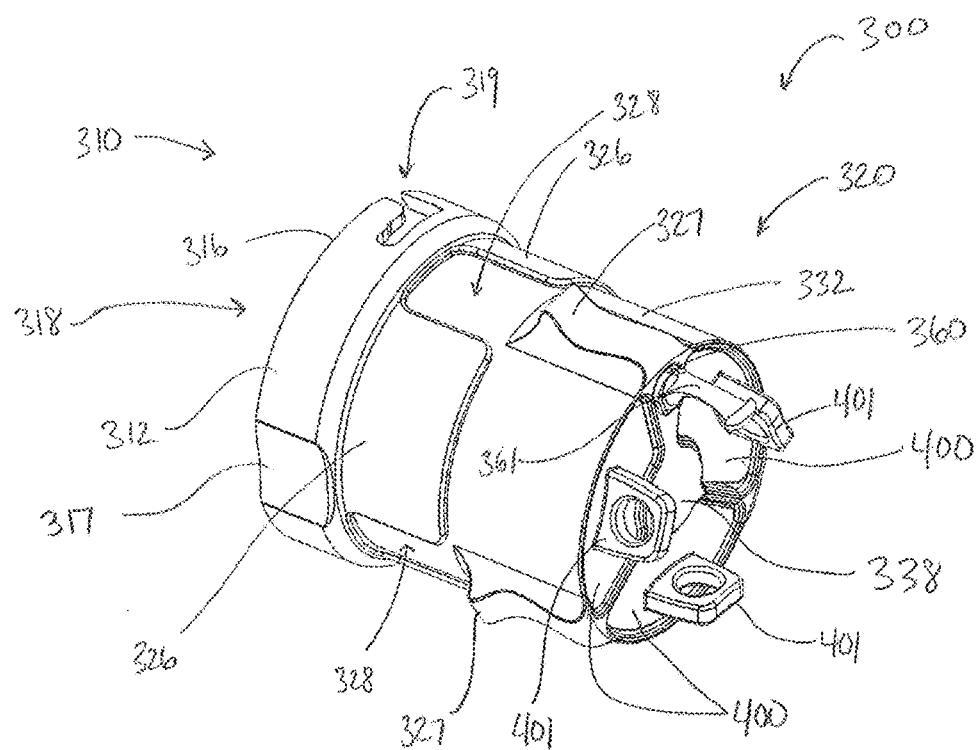
FIG. 3B depicts a perspective view of the tissue sample holder of FIG. 1 with the outer cup and the rotatable member slidably engaged thereto.

As best seen in FIGS. 3A-3B, tissue sample holder comprises an outer cup (310), a rotatable member (320), and a plug (360), and three bulk sample trays (400). As will be described in greater detail below, outer cup (310) is configured to receive rotatable member (320) therein. Rotatable member (320) is configured to slidably receive plug (360) within a plug chamber (348) and bulk sample trays (400) within a respective bulk tray chamber (350) (see FIG. 6). With this configuration, outer cup (310) is generally secured to probe (100) such that outer cup (310) remains fixed relative to probe (100) while rotatable member (320) and plug (360) and trays (400) rotate relative to outer cup (310) and probe (100). In this instance, as will be described in greater detail below, fluid management tube (106) extends into tissue sample holder (300) through a vacuum opening (354) (see FIGS. 4-5) such that fluid management tube (106) remains fixed relative to rotatable member (320) as rotatable member (320), plug chamber (348), and tray chambers (350) rotate about fluid management tube (106).

Outer cup (310) defines a generally cylindrical cup that is configured to receive rotatable member (320), as seen in FIG. 3B. In particular, outer cup (310) is a receiving channel that is sized and shaped to slidably and rotatably receive rotatable member (320) of tissue sample holder (300) therein. In other words, outer cup (310) serves as a fastening portion or engagement member that secures tissue sample holder (300) to biopsy device (10). Although, outer cup (310) of the present example is shown as a discrete part, it should be understood that in other examples outer cup (310) can be integrated into other components of biopsy device (10) such as probe (100).

Outer cup (310) comprises a cylindrical body (312), a distal rim (316) defining an open distal end (318), and a proximal flange (326) defining an open proximal end (324). Distal rim (316) further includes at least one grip feature (317) positioned along the surface of cylindrical body (312). In the present example, distal rim (316) includes a pair of grip features (317) positioned about cylindrical body (312). Alternatively, it should be understood that distal rim (316) may include numerous other configurations of grip features (317) as will be apparent to those of ordinary skill in the art. As will be described in greater detail below, grip features (317) provide an interface surface along cylindrical body (312) to facilitate grasping and rotating outer cup (310) for purposes of coupling and decoupling outer cup (310) to probe (100). Open distal end (318) is configured to communicate with the proximal end of cutter (130) to transport tissue samples from cutter (130) into trays (400).

In addition, distal rim (316) includes a plurality of fastening features (319) that are configured to engage the proximal end of probe (100) to thereby securely fasten outer cup (310) to probe (100). In the present example, distal rim (316) includes a pair of fastening feature (319) in the form of pin slots that are sized and shaped to receive a pair of fastening pins (not shown) of probe (100). Fastening features (319), in cooperation with fastening pins of probe (100), are operable to couple outer cup (310) to probe (100) via rotatable engagement between the fastening pins and fastening features (319). Alternatively, it should be understood that fastening features (319) may comprise other various suitable configurations and quantities as will be apparent to those of ordinary skill in the art. In other versions, outer cup (310) is unitarily formed with the proximal end of probe (100) such that outer cup (310) is integral with biopsy device (10). In this instance, outer cup (310) is securely attached to probe (100) and is configured to fasten tissue sample holder (300) to biopsy device (10). Although not shown, it should be understood that outer cup (310) may have other sizes, shapes, or profiles than those depicted.

As best seen in FIG. 3A, cylindrical body (312) of outer cup (310) is sized and shaped to receive rotatable member (320) through open proximal end (324). Distal rim (316) is configured to engage a distal edge (322) of rotatable member (320) such that outer cup (310) becomes securely fastened to rotatable member (320) when distal edge (322) abuts against distal rim (316). In some versions, distal edge (322) is configured to connect with distal rim (316) through a snap-fit engagement to thereby secure rotatable member (320) to outer cup (310). It should be understood that various other suitable engagement configurations and methods may be included as will be apparent to those of ordinary skill in the art. As will be described in greater detail below, with distal edge (322) coupled with distal rim (316), rotatable member (320) is operable to rotate relative to outer cup (310) by slidably moving distal edge (322) along the inner surface of distal rim (316).

Open proximal end (324) is defined by the proximal end of cylindrical body (312). Thus, it should be understood that open proximal end (324) is configured to receive rotatable member (320) proximally relative to outer cup (310). Proximal flange (326) is positioned adjacent to open proximal end (324) and extends proximally from cylindrical body (312). As will be described in greater detail below, proximal flange (326) is generally configured to receive distal edge (322) to rotatably fasten rotatable member (320) to outer cup (310). As will also be described in greater detail below, rotatable member (320) is configured to receive and hold a plurality of sample trays (400) therein. Thus, it should be understood that proximal flange (326) is configured to secure rotatable member (320), plug (360), and sample trays (400) to outer cup (310) while permitting rotation of rotatable member (320), plug (360), and sample trays (400) relative to outer cup (310).

Proximal flange (326) further includes a plurality of indexing features (328) angularly spaced apart such that the plurality of indexing features (328) are positioned around the perimeter of proximal flange (326). Indexing features (328) are generally configured to align with at least a portion of rotatable member (320) to position plug (360) trays (400) received within rotatable member (320) at certain predetermined positions. As will be described in greater detail below, each predetermined position generally corresponds to a given plug (360) or sample tray (400) being indexed with cutter (130). Although indexing features (328) of the present example are generally shown as gaps or openings in proximal flange (326), it should be understood that in other examples indexing features (328) may take on a variety of other forms.

Figure 4:
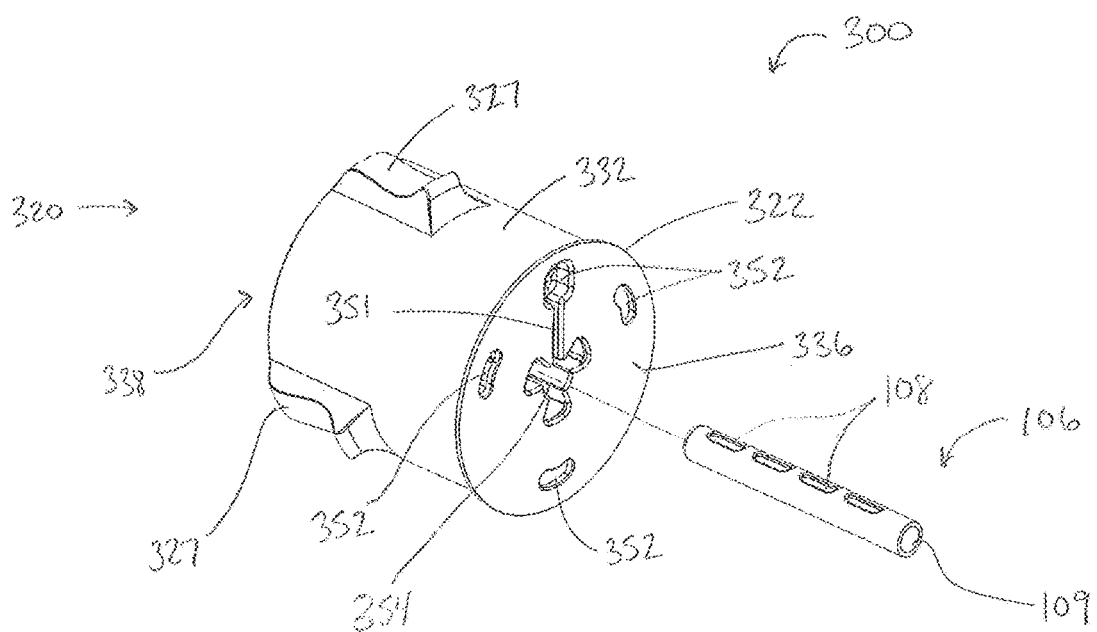
FIG. 4 depicts a perspective view of the tissue sample holder of FIG. 1 with the rotatable member aligned with the fluid management tube.

FIG. 4 shows rotatable member (320) comprising a cylindrical wall (332), a distal end (336), and a proximal end (338). Cylindrical wall (332) comprises a generally hollow cylindrical shape extending between distal end (336) and proximal end (338) with a plurality of grasp features (327) positioned thereon. As will be described in greater detail below, grasp features (327) provide an interface surface along cylindrical wall (332) to facilitate grasping and rotating rotatable member (320) relative to outer cup (310) for purposes of indexing tissue sample trays (400) with cutter (130) of needle (110). Although the presence of grasp features (327) herein implies rotation of rotatable member (320) by manual rotation, it should be understood that in other examples rotatable member (320) can be rotated by a motor or other automated rotation means.

Distal end (336) defines a generally closed end. To facilitate communication of vacuum and tissue samples from probe (100) into trays (400), distal end (336) defines a plurality of sample openings (352) and a vacuum opening (354). Sample openings (352) are positioned on distal end (336) of tissue sample holder (300) at locations that correspond with the angular position of sample trays (400) received within tissue sample holder (300). Sample opening (352) extends through distal wall (336) and into a corresponding tray opening (340, 342). Cutter (130) is in fluid communication with plug chamber (348) or a particular tray chamber (350) of tissue sample holder (300) when the corresponding sample opening (352) is rotatably aligned with cutter (130). In this instance, sample opening (352) is configured to receive tissue samples from cutter (130) such that the tissue sample is deposited within the respective sample tray (400) positioned within the corresponding tray chamber (350).

Rotatable member (320) further includes a vacuum opening (354) positioned centrally on distal wall (336) and extending into the inner region of rotatable member (320) between walls (336, 338). Vacuum opening (354) is sized and shaped to receive fluid management tube (106) therein when tissue sample holder (300) is coupled to probe (100). Vacuum opening (354) is generally in communication with the interior of rotatable member (320), particularly tray openings (340, 342). Vacuum opening (354) extends radially outward from a longitudinal axis (12) of rotatable member (320) toward a plurality of angular directions that correspond with the plurality of tray openings (340, 342) of tissue sample holder (300). In this instance, each tray opening (340, 342) is operable to communicate with vacuum opening (354) via vacuum opening (354) toward each respective tray opening (340, 342). As will be described in greater detail below, vacuum opening (354) permits communication of vacuum to tissue sample holder (300) to create a fluid circuit that pulls tissue samples from cutter (130) and into tissue sample holder (300). Additionally, in some circumstances, excess liquids such as blood, saline, etc. may be evacuated from tissue sample holder (300) via fluid management tube (106) positioned within vacuum opening (354).

Fluid management tube (106) of biopsy device (10) includes a plurality of lateral apertures (108) and a distal opening (109). Lateral apertures (108) extend along an outer surface of the length of fluid management tube (106). In the present example, lateral apertures (108) are aligned along a single axis of fluid management tube (106). Although not shown, it should be understood that in other versions lateral apertures (108) are aligned along multiple different axes of fluid management tube (106). Distal opening (109) is in fluid communication with probe (100), which thereby is in communication with a vacuum source (not shown). In this instance, fluid management tube (106) is configured to provide a vacuum into the particular tray chamber (350) that is indexed with lateral apertures (108) of fluid management tube (106) to thereby pull an extracted tissue sample through probe (100) and into tissue sample holder (300). In other words, distal opening (109) and lateral apertures (108) are configured to communicate a vacuum through the particular tray chamber (350) of tissue sample holder (300) that is aligned with cutter (130). Fluid management tube (106) is further operable to drain any fluids collected in the particular tray chamber (350) that is aligned with lateral apertures (108) such that the fluid drains into fluid management tube (106) by means of gravity or pressurized suction.

Figure 6:
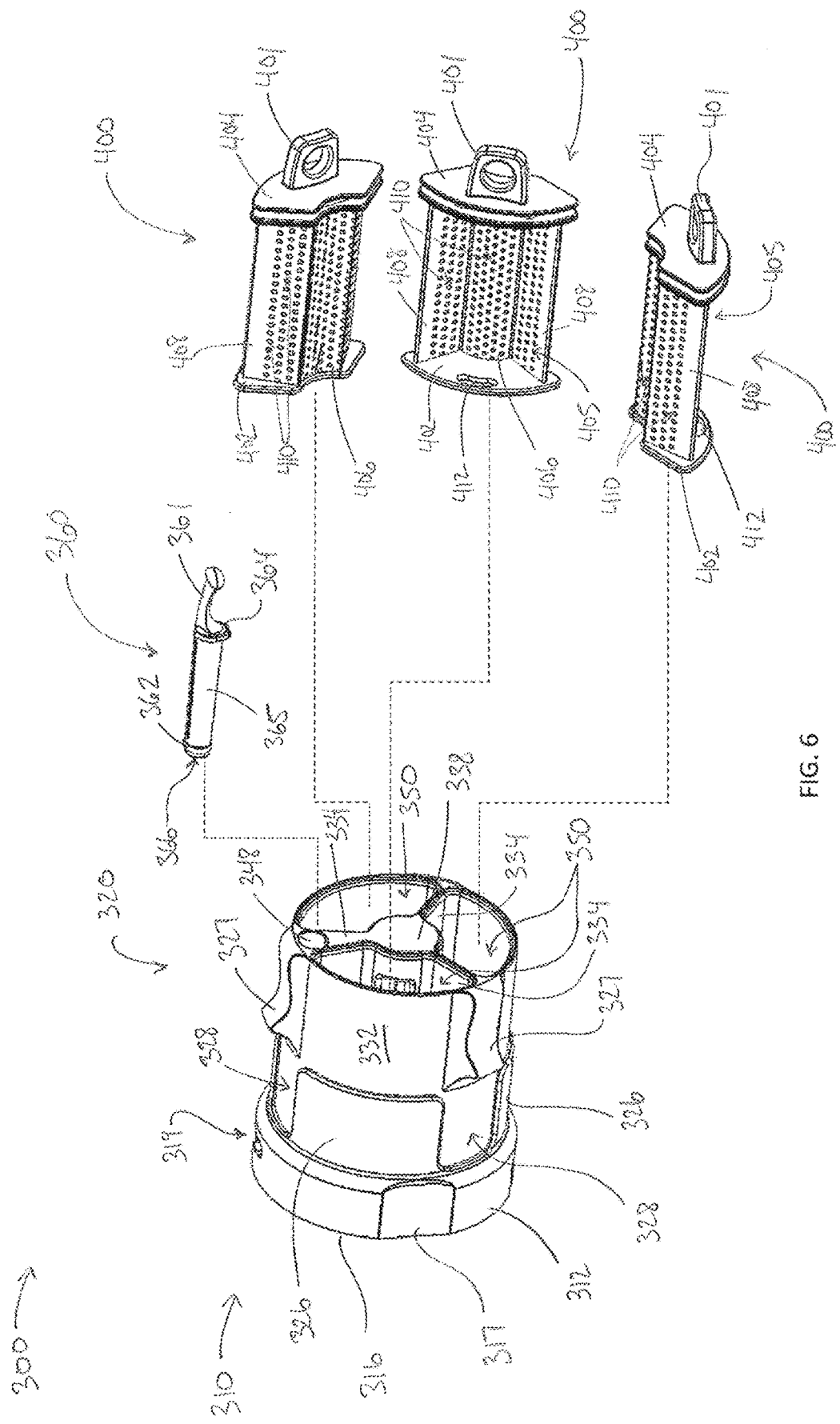
FIG. 6 depicts an exploded view of the tissue sample holder of FIG. 1, including a plurality of tray chambers and a plurality of tissue sample trays.
Figure 7:
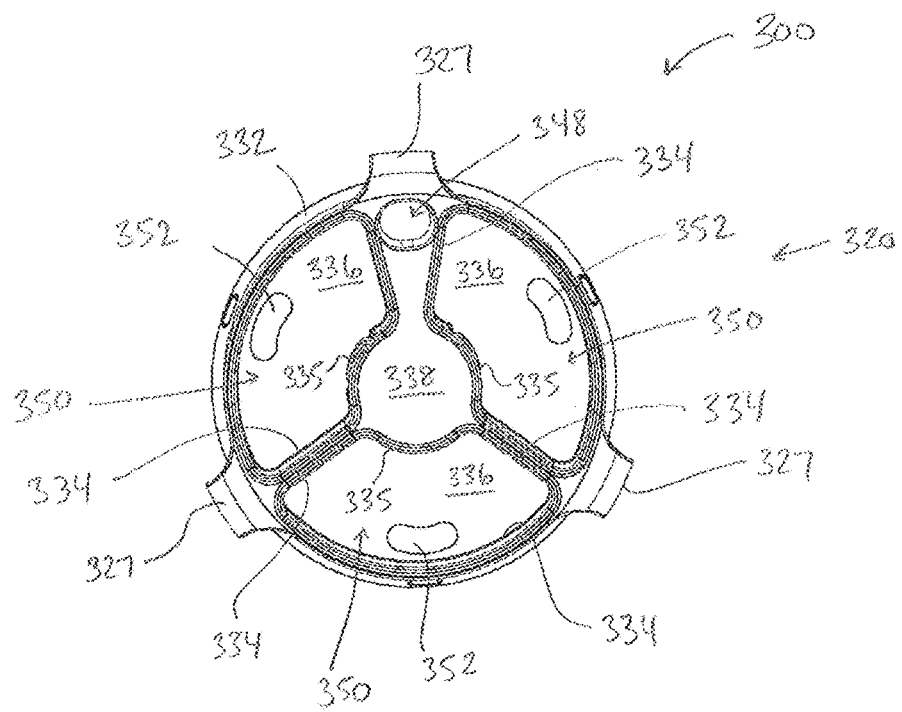
FIG. 7 depicts a front elevational view of the tissue sample holder of FIG. 1, with the plurality of tray chambers sized to receive the plurality of tissue sample trays.

FIG. 6 shows the interior of cylindrical wall (332) including a plurality of inner tray walls (334) extending from distal wall (336) to proximal wall (338). Each inner tray wall (334) also extends radially inwardly into the interior space defined by cylindrical wall (332), as best seen in FIG. 7. Thus, cylindrical wall (332) defines a single interior space that is at least partially divided by inner tray walls (334) protruding into the interior space. In other words, tray walls (334) serve as protrusions or space dividers within rotatable member (320). Inner tray walls (334) are angularly spaced around the interior circumference of cylindrical wall (332). The angular spacing of each tray wall (334) relative to an adjacent tray wall (334) corresponds to a width of either plug (360) or bulk sample tray (400). In addition, each tray wall (334) is integrated into cylindrical wall (332) by a radiused surface (335) such that each tray wall (334) progressively extends inwardly from the inner surface of cylindrical wall (332). Thus, two adjacent tray walls (334) and the radius of cylindrical wall (332) together define a semi-ovular shape that is configured to receive either plug (360) or bulk sample tray (400), depending on the angular separation between each adjacent tray wall (334). Because each tray wall (334) extends inwardly toward the center of cylindrical wall (332), it should be understood that each tray wall (334) is also configured to secure a corresponding plug (360) or bulk sample tray (400) to cylindrical wall (332), as will be described in greater detail below.

Proximal wall (338) is disposed on the proximal end of cylindrical wall (332), covering the proximal end of cylindrical wall (332). Although the proximal end of cylindrical wall (332) is generally closed by proximal wall (338), proximal wall (338) defines a plurality of openings (340, 342) therein. In particular, proximal wall (338) defines a single individual tray opening (340) and three bulk tray openings (342). Individual tray opening (340) is generally oval-shaped, as best seen in FIG. 7. Plug opening (340) provides access to plug chamber (348) of rotatable member (320), while bulk tray openings (342) provide access to bulk tray chambers (350), respectively. As will be described in greater detail below, plug opening (340) is configured to receive plug (360). Each bulk tray opening (342) is generally pie-shaped. As will also be described in greater detail below, each bulk tray opening (342) is configured to receive a single bulk sample tray (400). Although proximal wall (338) of the present example is shown as having a single individual tray opening (340) and three bulk tray openings (342), it should be understood that in other examples numerous other configurations can be used. For instance, in some examples proximal wall (338) defines a single bulk tray opening (342) and a plurality of individual tray openings (340). Of course, in other examples proximal wall (338) defines any other suitable number of individual tray openings (340) or bulk tray openings (342).

Bulk sample trays (400) comprise a distal tray wall (402) and a proximal tray wall (404) with a perforated chamber (405) extending therebetween. Perforated chamber (405) includes a base (406) and a pair of sidewalls (408) such that the base (406) is positioned between the sidewalls (408). Chamber (405) further includes a plurality of apertures (410) extending along base (406) and sidewalls (408) to thereby provide fluid communication through bulk sample tray (400). Base (406) is sized and shaped to correspond to the shape of radiused surface (335) of cylindrical wall (332) such that base (406) is configured to slidably fit along radiused surface (335) when bulk sample tray (400) is inserted into bulk tray chamber (350) of rotatable member (320). Similarly, sidewalls (408) are sized and shaped to correspond to the shape of tray walls (334) of cylindrical wall (332) such that sidewalls (408) are configured to slidably fit along tray walls (334) when bulk sample tray (400) is inserted into bulk tray chamber (350) of rotatable member (320).

Distal tray wall (402) has a corresponding sample opening (412) that is sized and shaped accordingly to associate with sample opening (352) of rotatable member (320). In other words, sample opening (412) is configured to align with sample opening (352) when bulk sample tray (400) is slidably inserted into bulk tray chamber (350) of rotatable member (320). In this instance, sample opening (412) of bulk sample trays (400) are operable to receive a tissue sample from probe (100) via the alignment with sample opening (352). Proximal tray wall (404) includes a handle (401) extending proximally therefrom. Handle (401) is shaped and sized to be grasped by a user to thereby provide selective manipulation of bulk sample tray (400). In particular, handle (401) is operable to slidably guide bulk sample tray (400) into bulk tray chamber (350) of rotatable member (320), and alternatively, to retract bulk sample tray (400) from rotatable member (320).

Plug (360) comprises an elongate body (365) extending between a distal end (366) and a handle (361). Body (365) includes a distal seal (362) and a proximal seal (364) for engaging the interior of plug chamber (348). Handle (361) extends proximally from body (365). Similar to handle (401) of bulk sample tray (400), handle (361) is shaped and sized to be grasped by a user to thereby provide selective manipulation of plug (360). In particular, handle (361) is operable to guide plug (360) into plug chamber (348) of rotatable member (320), and alternatively, to plug (360) from rotatable member (320).

Although plug chamber (348) is described herein as being used to receive plug (360), it should be understood that in other examples plug chamber (348) can also receive an individual sample tray (not shown) in lieu of plug (360). Such an individual sample tray can be used to similarly to bulk sample trays (400) described above, except only a single sample may be collected in such an individual sample tray for sample analysis purposes. Suitable individual sample trays can comprises a distal tray wall, a proximal tray wall with an elongated chamber extending therebetween. Suitable elongated chambers can be sized and shaped to receive an individual tissue sample therein. Suitable distal tray walls can include includes a sample opening sized and shaped to receive a tissue sample. Thus, suitable sample openings can be configured to receive a tissue sample from probe (100) via the alignment with the sample opening (352) associated with plug chamber (348).

Figure 9:
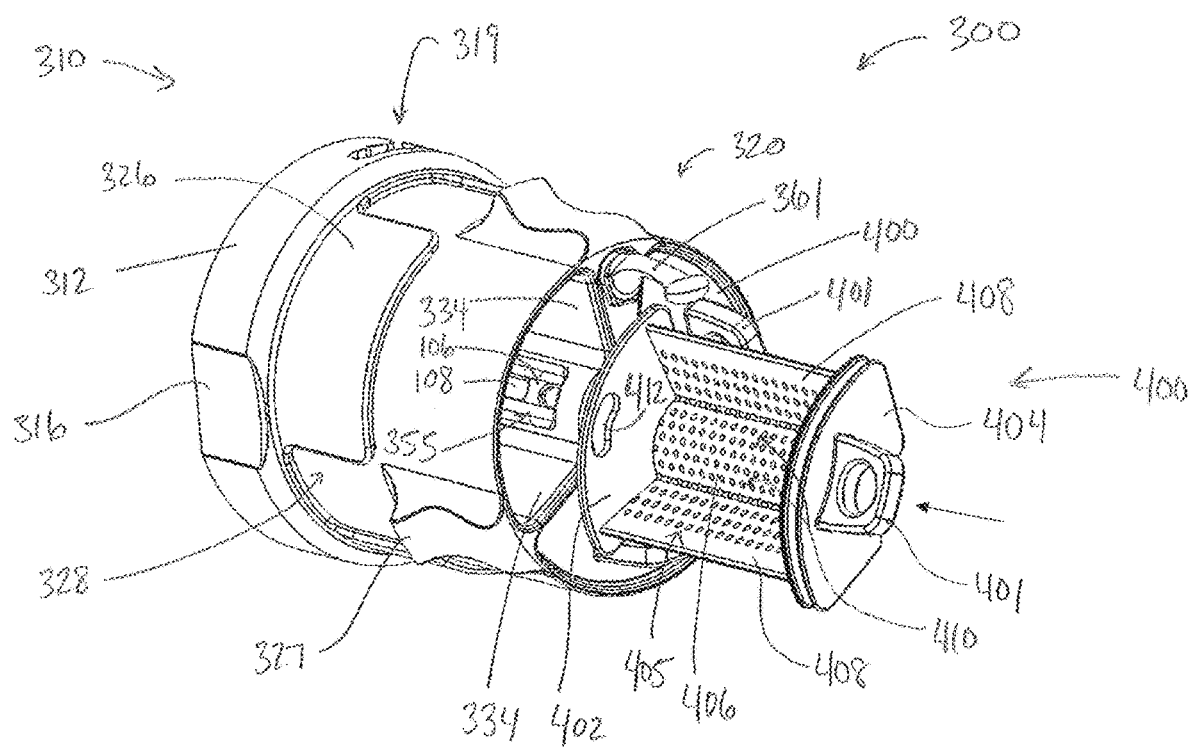
FIG. 9 depicts a perspective view of the tissue sample holder of FIG. 1 with the plurality of tissue sample trays received within the plurality of chamber openings.

As best seen in FIG. 7, plug plug opening (340) and each bulk tray opening (342) are positioned to be adjacent to two corresponding tray walls (334) of cylindrical wall (332). In particular, plug opening (340) is positioned with a corresponding tray wall (334) adjacent to each outer corner of the oval shape of individual tray opening (340). Similarly, each bulk tray opening (342) is positioned with a corresponding tray wall (334) adjacent to each outer corner of the general pie shape of each bulk tray opening (342). As seen in FIG. 9, this configuration generally permits tray wall (334) to act as tracks or retaining features for plug (360) or each bulk sample tray (400) as trays (360, 400) are received within a corresponding tray opening (340, 342), respectively.

Figure 5:
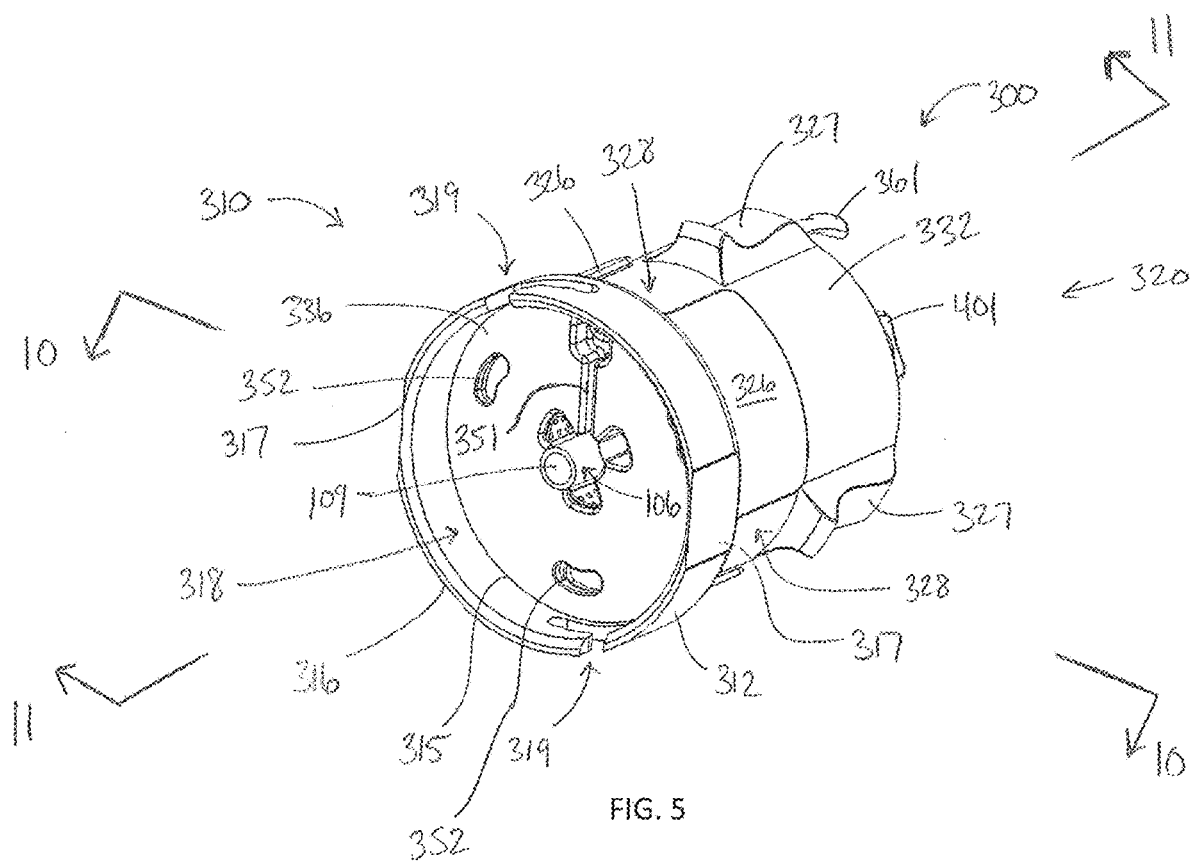
FIG. 5 depicts a perspective view of the tissue sample holder of FIG. 1 with the fluid management tube received within the rotatable member.

Plug (360) generally prevents the flow of vacuum proximally through rotatable member (320). To promote the flow of vacuum in the presence of plug (360) from fluid management tube (106) to cutter (130), rotatable member (320) defines a fluid short-cut or bypass (351) located on distal wall (336), as seen in FIG. 4. In the present example, fluid bypass (351) is formed by a recessed channel that extends between vacuum opening (354) and the sample opening (352) associated with plug (360) such that fluid management tube (106) is operable to communicate vacuum directly into cutter (130) via fluid bypass (351) when fluid management tube (106) is positioned within vacuum opening (354), as seen in FIG. 5. Although not shown, it should be understood that in other examples fluid bypass (351) can be omitted in favor of other alternative fluid passages. For instance, as described above, in some examples an individual sample tray can be used in lieu of plug (360). In such examples, it may be desirable to direct vacuum into the individual sample tray rather than directly into cutter (130). Accordingly, in some examples plug chamber (348) can be in direct communication with fluid management tube (106).

Figure 8:
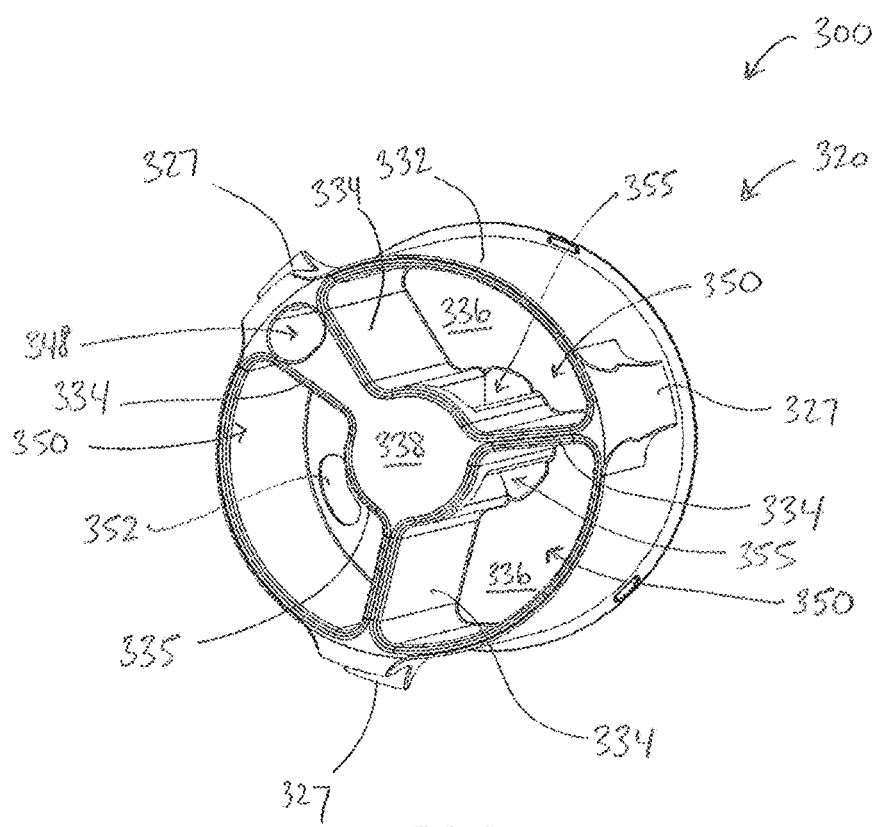
FIG. 8 depicts a perspective view of the tissue sample holder of FIG. 1, with the plurality of tray chambers having an inner aperture for communication with the fluid management tube received within the rotatable member.

Bulk sample trays (400) are in communication with vacuum opening (354) via a tray aperture (355) located within each bulk sample tray (400). As best seen in FIG. 8, tray aperture (355) extends between distal end (336) and proximal wall (338) along the inner tray wall (334) that is proximate to vacuum opening (354). Accordingly, with tissue sample holder (300) coupled to probe (100), fluid management tube (106) extends into vacuum opening (354) such that a particular tray chamber (350) is indexed with lateral apertures (108). In this instance, as shown in FIG. 9, bulk tray chamber (350) is aligned with lateral apertures (108) of fluid management tube (106) such that the bulk sample tray (400) that is slidably received therein will be in communication with probe (100). In this instance, with bulk sample tray (400) indexed with fluid management tube (106), sample opening (352) of bulk tray chamber (350) is also aligned with needle (110) such that the bulk sample tray (400) received therein will receive any tissue samples extracted by cutter (130).

III. Exemplary Use

In exemplary use, tissue sample holder (300) is coupled to probe (100) by assembling outer cup (310) onto the proximal end of probe (100) via the engagement of fastening features (319) with corresponding fastening features of probe (100) such that fluid management tube (106) extends through open proximal end (324) of outer cup (310). In this instance, rotatable member (320) is then slidably inserted into open proximal end (324) such that cylindrical wall (332) is received within cylindrical body (312) and proximal flanges (326) of outer cup (310). Rotatable member (320) is advanced distally through open proximal end (324) until distal edge (322) of rotatable member (320) engages distal rim (316) of outer cup (310). In this instance, with distal edge (322) interlocked with track (315) of distal rim (316), rotatable member (320) is securely coupled to outer cup (310) such that fluid management tube (106) of probe (100) is received within vacuum opening (354). Alternatively, it should be understood that rotatable member (320) may be coupled to outer cup (310) prior to fastening outer cup (310) to probe (100). In this instance, tissue sample holder (300) is coupled to probe (100) as a completed assembly such that fluid management tube (106) is aligned with vacuum opening (354) of rotatable member (320) prior to fastening features (319) of outer cup (310) engaging the corresponding fastening features of probe (100).

Figure 10A:
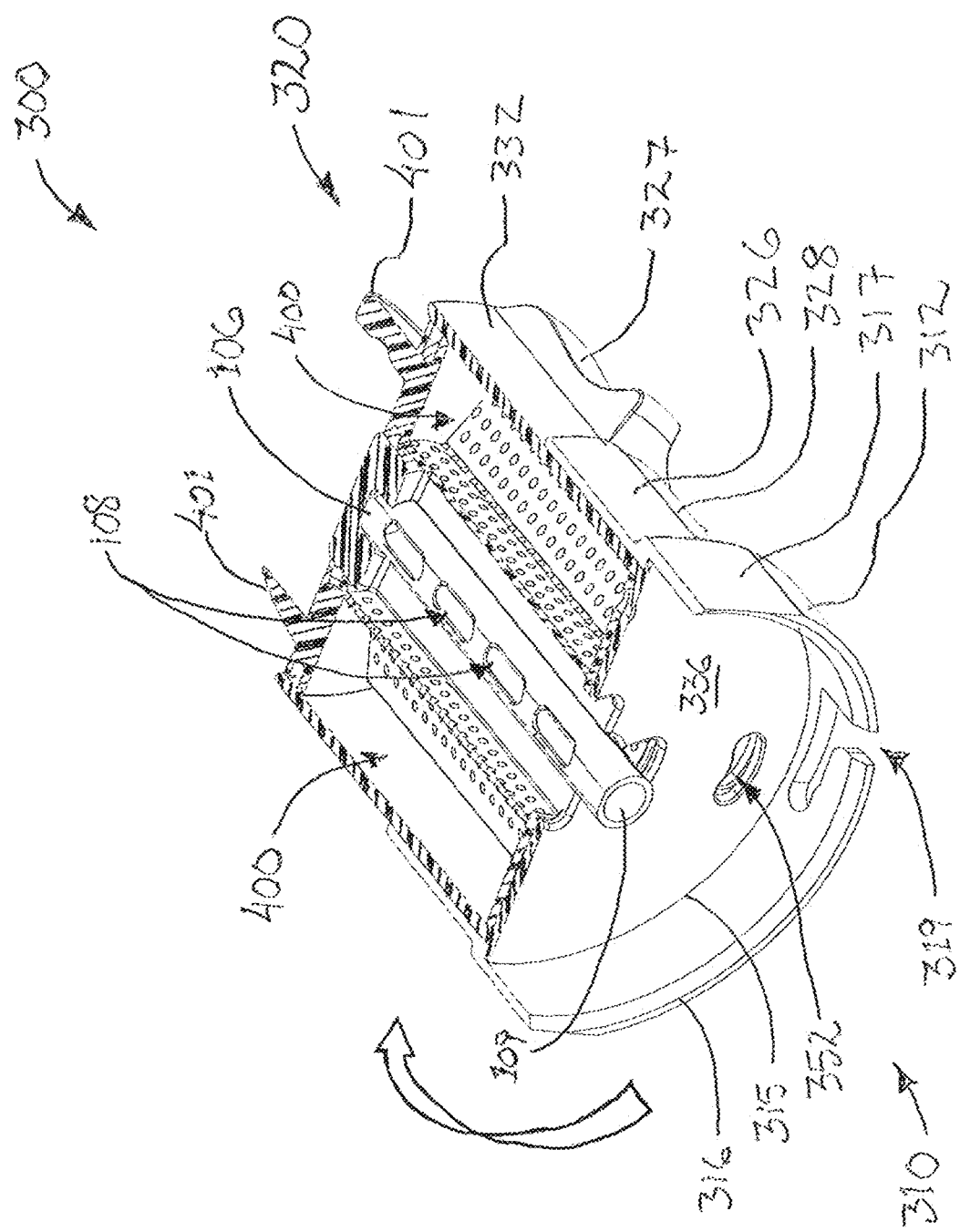
FIG. 10A depicts a cross-sectional view of the tissue sample holder of FIG. 1 in a first rotatable position relative to the fluid management tube positioned therein, with the plurality of tissue sample trays received within the plurality of chamber openings, the cross-section taken along line 10-10 of FIG. 5.

As seen in FIG. 10A, sample trays (400) may be inserted into tray chambers (350) through tray openings (342) prior to the coupling of rotatable member (320) and outer cup (310). In this instance, tissue sample holder (300) is operable to receive tissue samples (11) extracted by biopsy device (10). Alternatively, it should be understood that sample trays (400) may be received within chambers (350) at any other point after rotatable member (320) is attached to outer cup (310) as will be apparent to those of ordinary skill in the art. In this instance, tissue sample holder (300) must subsequently receive one or more sample trays (400) therein prior to commencing use of biopsy device (10) to extract tissue samples (11) with cutter (130).

Although rotatable member (320) depicts three bulk tray chambers (350) and a single plug chamber (348), it should be understood that rotatable member (320) may include numerous varying configurations of chambers (348, 350) therein. With rotatable member (320) received within outer cup (310), rotatable member (320) is effectively in communication with probe (100) through outer cup (310). In this instance, the particular plug chamber (348) or tray chamber (350) that is aligned with needle (110) is thereby in fluid communication with cutter (130) of probe (100). Accordingly, the sample tray (400) received within the particular tray chamber (350) that is aligned with needle (110) is also in fluid communication with cutter (130) such that that sample tray (400) is operable to receive any tissue samples (11) extracted by biopsy device (10). Further, the sample tray (400) received within the particular tray chamber (350) that is aligned with needle (110) is simultaneously in communication with lateral apertures (108) of fluid management tube (106) via vacuum opening (354). In this instance, a vacuum source (not shown) may be activated to communicate vacuum through the tissue sample chamber (350) that is aligned with lateral apertures (108) to thereby pull a tissue sample (11) that was recently extracted by cutter (130) through needle (110) and into the sample tray (400) positioned within sample chamber (350).

Figure 11:
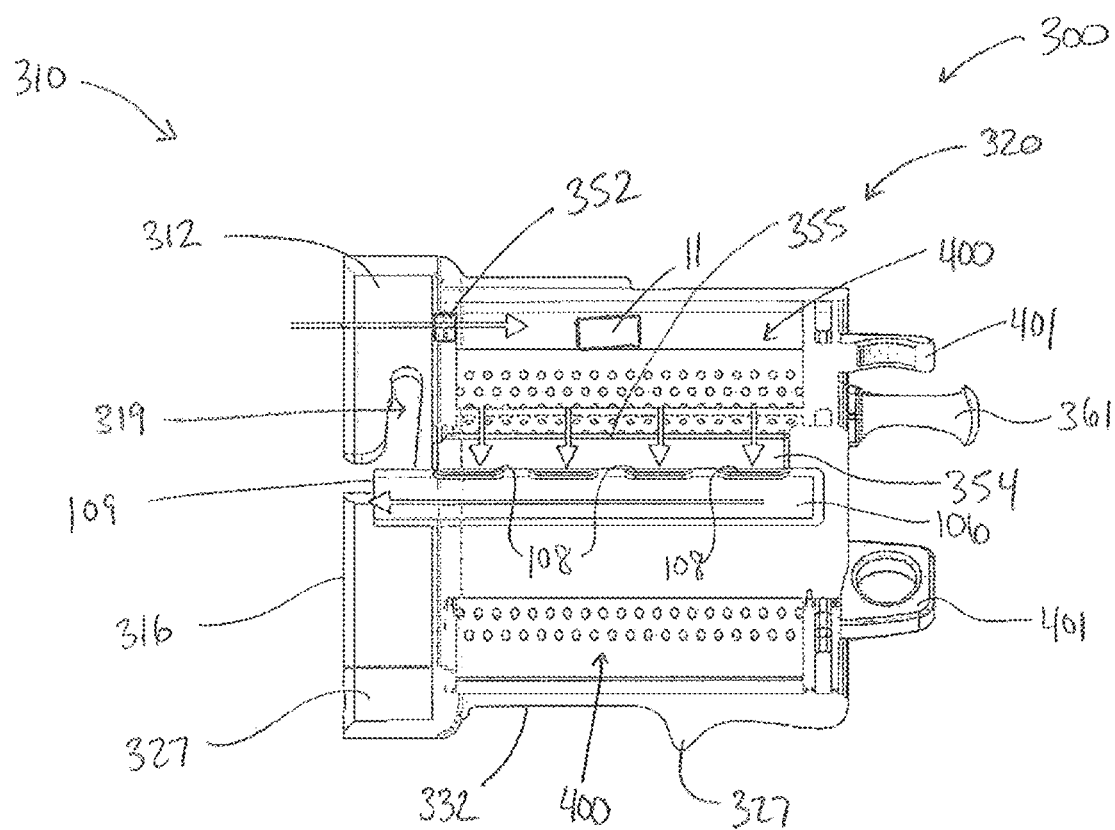
FIG. 11 depicts a cross-sectional view of the tissue sample holder of FIG. 1, with a tissue sample deposited within the tissue sample tray, the cross-section taken along line 11-11 of FIG. 5.

In other words, the vacuum source is coupled to probe (100) and communicates a vacuum to tissue sample holder (300) via the fluid management tube (106) that is axially disposed within vacuum opening (354) of rotatable member (320). In particular, the vacuum is transmitted into sample chambers (350) through lateral apertures (108) such that the particular sample opening (352) of the sample chamber (350) that is currently aligned with needle (110) conveys the vacuum pressure through probe (100) and to needle (110) to thereby pull the tissue sample (11) deposited within needle (110) proximally into sample tray (400) as seen in FIG. 11. In the present example, bulk tray chamber (350) is aligned with lateral apertures (108) of fluid management tube (106) such that any tissue samples (11) extracted by cutter (130) are thereby communicated into the bulk sample tray (400) received within that bulk tray chamber (350) via sample opening (352). An operator may extract and deposit multiple tissue specimens into bulk sample tray (400) due to the size of bulk sample tray (400). Further, fluid management tube (106) will receive any excess fluid from the tissue samples (11) deposited within bulk sample tray (400) via lateral apertures (108) while that particular bulk tray chamber (350) remains aligned with lateral apertures (108). In this instance the fluid is transmitted through distal opening (109) of fluid management tube (106) and into probe (100), as best seen in FIG. 11.

Once bulk sample tray (400) has received a desirable quantity of tissue samples (11) therein, an operator may grasp grip features (327) of rotatable member (320) to thereby rotate rotatable member (320) relative to outer cup (310) and probe (100). In this instance, as seen in FIG. 10B, distal edge (322) slidably rotates within track (315) of distal rim (316) until an operator indexes a subsequent tray chamber (350) into alignment with cutter (130) of needle (110). An operator receives visual feedback from tissue sample holder (300) that a subsequent tray chamber (350) is indexed into alignment with cutter (130) via the location of indexing features (328) relative to proximal flanges (326). In particular, rotating rotatable member (320) about fluid management tube (106) provides for the simultaneous movement of indexing features (326) relative to proximal flanges (326) of outer cup (310) such that indexing features (328) are operable to indicate to an operator the relative location of tray chambers (350) to cutter (130). In other words, fluid management tube (106) remains fixed in place as rotatable member (320) rotates about fluid management tube (106) such that lateral apertures (108) of fluid management tube (106) maintain the same directional orientation within rotatable member (320) as tray chambers (350) and sample trays (400) rotate. In this instance, only the tray aperture (355) of the particular tray chamber (350) that is currently, rotatably aligned with lateral apertures (108) will be in communication with fluid management tube (106) since fluid management (106) is rotatably fixed to probe (100) as rotatable member (320) rotates. With the orientation of fluid management tube (106) securely fixed within tissue sample holder (300), fluid management tube (106) is capable of communicating a vacuum directly into the particular tray chamber (350) that is currently indexed with lateral apertures (108) through tray aperture (355) to thereby improve fluid flow between the sample tray (400) received therein and fluid management tube (106). This improved fluid flow is a result of the vacuum flow transmitted by fluid management tube (106) being exclusively concentrated to only the particular tray chamber (350) that is currently indexed with lateral apertures (108), rather than all tray chambers (350) being in communication with fluid management tube (106) simultaneously even when those chambers (350) don't require vacuum.

Accordingly, an operator rotates rotatable member (320) in either direction, clockwise or counterclockwise, until a desired tray chamber (350) is aligned with needle (110). Although not shown, it should be understood that tissue sample holder (300) may further include other feedback features to indicate to an operator when a subsequent tray chamber (350) is in communication with needle (110). By way of example only, tissue sample holder (300) may provide a tactile feedback or various other suitable indicators as will be apparent to those of ordinary skill in the art. An operator may continue the performing the steps outlined above until the desired number of tissue samples (11) have been extracted by cutter (130) and subsequently deposited within sample trays (400) respectively. During the procedure, or after completion of the procedure, an operator may manipulate handles (361, 401) of sample trays (400), respectively, to remove a given sample tray (400) from its respective tray chamber (350) to thereby inspect and/or access the tissue samples (11) contained therein. Alternatively, an operator may removably decouple rotatable member (320) from outer cup (310) prior to accessing the tissue samples (11) deposited within sample trays (400). In still another version, an operator may detach outer cup (310) from probe (100) by disengaging fastening features (319) of outer cup (310) from the corresponding fastening features of probe (100) prior to accessing the tissue samples (11) deposited within tissue sample holder (300). In either instance, pulling handle (361, 401) in a proximal direction relative to tissue sample holder (300) causes the removal of sample tray (400) from within tray chamber (350) such that the tissue samples (11) contained therein are exposed and readily accessible for inspection and analysis.

At any point during the procedure described above, an operator may desire to use plug chamber (348). For instance, after one or more tissue samples have been collected within one or more bulk sample trays (400), an operator may desire to mark the biopsy site or introduce therapeutic substances using plug chamber (348). At this stage, an operator can rotate rotatable member (320) to index plug chamber (348) with cutter (130). Plug (360) can then be removed via handle (361), thereby providing access to cutter (130) via plug chamber (348). The operator can then use plug chamber (348) to introduce a maker delivery instrument or a syringe for the introduction of therapeutic substances. Once a marker or therapeutic substance is delivered, an operator can replace plug (360) and either continue collecting biopsy samples or conclude the procedure.

As described above, in some instances it may be desirable to use plug chamber (348) to contain an individual sample tray in lieu of plug (360). In such examples, the individual sample tray can be used at various stages during the procedure described above. For instance, in some uses the individual sample tray can be used prior to the collection of tissue samples within any of bulk sample trays (400). This may include collecting an individual tissue sample within the individual sample tray and then removing the individual sample tray to inspect the collected sample. This may be desirable to perform an initial assessment of the first collected sample to determine whether samples are being collected from a suspicious lesion. Once the initial sample is confirmed, an operator can then replace the individual sample tray and rotate rotatable member to index the next successive bulk sample tray (400) with cutter to collect tissue samples in bulk. In addition, or in the alternative, the individual sample tray may be used periodically through the procedure to confirm whether the samples being collected are still desirable. In such uses, rotatable member (320) can be rotated to index plug chamber (348) with cutter (130) for collection of an individual sample within the individual sample tray. Once the assessment is complete, rotatable member (320) can be rotated to resume collection of tissue samples in bulk via bulk sample trays (400).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

An instrument, comprising: (a) a body assembly, wherein the body assembly includes an axial tube extending proximally from a proximal end of the body assembly, wherein the axial tube includes at least one aperture; (b) a needle assembly extending distally from the body assembly, wherein the needle assembly includes a needle and a cutter movable relative to the needle; and (c) a tissue sample holder assembly configured to removably couple to a proximal end of the body assembly such that the axial tube is disposed within the tissue sample holder assembly, wherein at least a portion of the tissue sample holder assembly is rotatable relative to the body assembly such that the tissue sample holder assembly is configured to rotate about the axial tube, wherein the tissue sample holder assembly is in fluid communication with the axial tube via the at least one aperture.

EXAMPLE 2

The instrument of Example 1, wherein the tissue sample holder assembly includes a manifold that defines a plurality of tray chambers.

EXAMPLE 3

The instrument of Example 2, wherein the plurality of tray chambers includes at least one individual tray chamber and at least one bulk tray chamber.

EXAMPLE 4

The instrument of Example 3, wherein the at least one individual tray chamber is sized and configured to hold the at least one individual sample tray.

EXAMPLE 5

The instrument of Example 3, wherein the at least one bulk tray chamber is sized and configured to hold the at least one bulk sample tray.

EXAMPLE 6

The instrument of Example 5, wherein the tissue sample holder includes one individual sample chamber and three bulk sample chambers.

EXAMPLE 7

The instrument of Example 1, wherein the tissue sample holder assembly is configured to receive a plurality of sample trays.

EXAMPLE 8

The instrument of Example 7, wherein the plurality of tray chambers are sized and shaped to slidably receive the plurality of sample trays therein.

EXAMPLE 9

The instrument of Example 7, wherein the plurality of sample trays includes at least one individual sample tray and at least one bulk sample tray.

EXAMPLE 10

The instrument of Example 9, wherein the individual sample tray is sized and configured to receive one tissue sample therein.

EXAMPLE 11

The instrument of Example 9, wherein the bulk sample tray is sized and configured to receive a plurality of tissue samples therein.

EXAMPLE 12

The instrument of any one or more of Examples 1 through 11, wherein the body assembly is coupled to a vacuum source, wherein the vacuum source is configured to generate a vacuum through the body assembly.

EXAMPLE 13

The instrument of Example 12, wherein the tissue sample holder assembly is in communication with the vacuum source through the at least one aperture of the axial tube.

EXAMPLE 14

The instrument of any one or more of Examples 7 through 13, wherein the axial tube is in fluid communication with the plurality of sample chambers such that the at least one aperture is configured to communicate with an indexed sample chamber of the plurality of sample chambers, wherein the indexed sample chamber is aligned with the axial tube based on a rotatable alignment of the tissue sample holder assembly relative to the body assembly.

EXAMPLE 15

The instrument of Example 1, wherein the axial tube is fixedly attached to the body assembly such that the axial tube is rotatably fixed.

EXAMPLE 16

The instrument of Example 1, wherein the tissue sample holder assembly includes a plurality of grip features, wherein the plurality of grip features are configured to selectively manipulate a rotatable orientation of the tissue sample holder assembly relative to the body assembly.

EXAMPLE 17

The instrument of Example 1, wherein the tissue sample holder assembly includes an indexing mechanism, wherein the indexing mechanism is operable to generate a feedback of a rotatable orientation of the tissue sample holder assembly relative to the body assembly.

EXAMPLE 18

The instrument of Example 1, wherein the tissue sample holder assembly includes one or more fastening features, wherein the body assembly includes one or more corresponding fastening features.

EXAMPLE 19

The instrument of Example 18, wherein the one or more fastening features of the tissue sample holder assembly is configured to mate with the one or more corresponding fastening features of the body assembly to thereby securely couple the tissue sample holder assembly to the body assembly.

EXAMPLE 20

The instrument of Example 1, wherein the tissue sample holder assembly is configured to receive tissue samples extracted by the cutter.

EXAMPLE 21

The instrument of Example 1, wherein the axial tube is coaxial with the tissue sample holder assembly such that the axial tube defines an axis of rotation of the tissue sample holder assembly.

EXAMPLE 22

A biopsy device, comprising: (a) a body; (b) a fluid management feature extending proximally from the body; (c) a needle extending distally from the body; and (d) a tissue sample holder removably coupled to the body, wherein the fluid management conduit is coaxially disposed within the tissue sample holder when the tissue sample holder is coupled to the body, wherein at least a portion of the tissue sample holder is configured to rotate relative to the fluid management conduit when coupled to the body, wherein the fluid management conduit is configured to be fixedly stationary within the tissue sample holder in response to rotation of the at least a portion of the tissue sample holder, wherein the fluid management conduit is configured to provide fluid communication between the body and the tissue sample holder.

EXAMPLE 23

An instrument, comprising: (a) a body; (b) a fluid tube extending proximally from the body; (c) a needle extending distally from the body; and (d) a tissue sample holder selectively attached to the body, wherein the fluid tube is coaxially disposed within the tissue sample holder when the tissue sample holder is coupled to the body, wherein at least a portion of the tissue sample holder is configured to rotate about the fluid tube when attached to the body such that the fluid tube is fixed relative to the tissue sample holder while at least a portion of the tissue sample holder is rotatable relative to the fluid tube, wherein the fluid tube is in fluid communication with the body and the tissue sample holder.

EXAMPLE 24

An instrument, comprising: (a) body assembly; (b) a needle extending distally from the body assembly; (c) a fluid management tube extending proximally from the body assembly, wherein the fluid management tube includes at least one fluid aperture; and (d) a tissue holder assembly rotatably engaged to a proximal end of the body assembly such that the fluid management tube is in fluid communication with the tissue holder assembly, wherein the tissue holder assembly includes a plurality of tray walls integrally formed within an interior space of the tissue holder assembly, wherein the plurality of trays walls are configured to removably receive a plurality of tissue sample trays such that the plurality of tissue sample trays are separated from an adjacent tissue sample tray by the plurality of tray walls, wherein the plurality of tissue sample trays include a plurality of perforations along a tray surface of the plurality of tissue sample trays, wherein the fluid management tube is configured to fluidly communicate with the plurality of tissue sample trays by the plurality of perforations when the tissue holder assembly is engaged to the body assembly, wherein the at least one fluid aperture of the fluid management feature is configured to receive fluid from the tissue sample tray of the plurality of tissue sample trays that is rotatably aligned with the at least one aperture via the plurality of perforations.

EXAMPLE 25

A method of using a biopsy device, the biopsy device including: (a) body assembly, (b) a needle extending distally from the body assembly; (c) a fluid management tube extending proximally from the body assembly, wherein the fluid management tube includes at least one fluid aperture; and (d) a tissue holder assembly rotatably engaged to a proximal end of the body assembly such that the fluid management tube is coupled to the tissue holder assembly, wherein the tissue holder assembly is configured to removably receive a plurality of tissue sample trays, wherein the fluid management tube is configured to fluidly communicate with the plurality of tissue sample trays when the tissue holder assembly is engaged to the body assembly, wherein the at least one fluid aperture of the fluid management feature is configured to receive fluid from the tissue sample tray of the plurality of tissue sample trays that is rotatably aligned with the at least one aperture; wherein the method comprises: (a) coupling the tissue holder assembly to the body assembly such that the fluid management tube is coaxially disposed within the tissue holder assembly, (b) rotating the tissue holder assembly to align a first tissue sample tray of the plurality of tissue sample trays with the needle such that the first tissue sample tray is in fluid communication with the needle, (c) collecting a tissue sample with the needle, (d) transmitting the tissue sample toward the tissue holder assembly and into the first tissue sample tray, (e) suctioning fluid from the first tissue sample tray through the fluid management tube, and (f) rotating the tissue holder assembly to align a second tissue sample tray of the plurality of tissue sample trays with the needle.

V. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A biopsy device, comprising:
   (a) a body defining a proximal end;
   (b) a fluid conduit extending proximally from the proximal end of the body, the fluid conduit defining at least one aperture;
   (c) a needle assembly extending distally from the body, the needle assembly including a needle and a cutter movable relative to the needle; and
   (d) a tissue sample holder adapted to couple to the proximal end of the body such that the fluid conduit is disposed within the tissue sample holder, at least a portion of the tissue sample holder being rotatable relative to the body such that the tissue sample holder is configured to rotate about the fluid conduit, the tissue sample holder being in fluid communication with the fluid conduit through the at least one aperture, the fluid conduit defining a plurality of apertures spaced on an outer surface of the fluid conduit, the plurality of apertures being aligned along a single axis.

2. The biopsy device of claim 1, the tissue sample holder including a manifold that defines a plurality of tray chambers, the fluid conduit extending through the manifold to communicate vacuum to a selected tray chamber of the plurality of tray chambers.

3. The biopsy device of claim 1, the tissue sample holder including a manifold that defines a plurality of tray chambers, the plurality of tray chambers including at least one individual tray chamber and at least one bulk tray chamber.

4. The biopsy device of claim 3, the at least one individual tray chamber is being sized and configured to hold an individual sample tray.

5. The biopsy device of claim 3, the at least one bulk tray chamber being sized and configured to hold a bulk sample tray.

6. The biopsy device of claim 5, the tissue sample holder including a single individual sample chamber and three bulk sample chambers.

7. The biopsy device of claim 1, the tissue sample holder being configured to receive a plurality of sample trays, the plurality of sample trays including at least one individual sample tray and at least one bulk sample tray.

8. The biopsy device of claim 7, the individual sample tray being configured to receive a single tissue sample therein.

9. The biopsy device of claim 7, the bulk sample tray being sized and configured to receive a plurality of tissue samples therein.

10. The biopsy device of claim 1, the body being adapted to couple to a vacuum source such that the body is configured to provide vacuum to the fluid conduit from the vacuum source.

11. The biopsy device of claim 10, the tissue sample holder being in communication with the vacuum source through the at least one aperture of the fluid conduit.

12. The biopsy device of claim 10, the tissue sample holder defining a plurality of sample chambers, wherein the fluid conduit being configured to align with each sample chamber of the plurality of sample chambers such that the at least one aperture is configured to communicate vacuum from the vacuum source to each sample chamber of the plurality of sample chambers.

13. The biopsy device of claim 1, the fluid conduit being rotatably fixed relative to the body.

14. The biopsy device of claim 1, the fluid conduit being coaxial with the tissue sample holder such that the fluid conduit defines an axis of rotation of the tissue sample holder.

15. A biopsy device, comprising:
   (a) a body;
   (b) a fluid management conduit extending proximally from the body, the fluid management conduit defining a plurality of apertures;
   (c) a needle extending distally from the body; and
   (d) a tissue sample holder rotatably coupled to the body, the fluid management conduit being coaxially disposed within the tissue sample holder, at least a portion of the tissue sample holder being configured to rotate relative to the fluid management conduit when coupled to the body, the fluid management conduit being configured to be fixedly stationary within the tissue sample holder in response to rotation of the at least a portion of the tissue sample holder with the plurality of apertures oriented in a common direction relative to the at least a portion of the tissue sample holder, the fluid management conduit being configured to provide fluid communication between the body and the tissue sample holder.

16. The biopsy device of claim 15, the plurality of apertures of the fluid management conduit being aligned along a single axis.

17. The biopsy device of claim 15, the tissue sample holder including a rotatable member defining a plurality of tray cavities oriented around a central vacuum cavity, the fluid management conduit being disposed within the vacuum cavity when the tissue sample holder is coupled to the body.

18. The biopsy device of claim 15, the tissue sample holder including a rotatable member defining a plurality of tray cavities oriented around a central vacuum cavity, the fluid management conduit being disposed within the vacuum cavity when the tissue sample holder is coupled to the body, the plurality of apertures of the fluid management conduit being aligned along a single axis and evenly spaced along the single axis.

19. A biopsy device, the biopsy device comprising:
(a) probe having a proximal coupler;
(b) a fluid management tube extending proximally from the proximal coupler of the probe, the fluid management tube including at a plurality of lateral apertures, the plurality of lateral apertures oriented in a single direction relative to an outer surface of the fluid management tube; and
(d) a tissue sample holder having a manifold rotatably engaged to the proximal coupler of the probe such that the fluid management tube extends proximally into the manifold, the manifold being configured to removably receive a plurality of tissue sample trays, the fluid management tube being configured to fluidly communicate with a selected tissue sample tray of the plurality of tissue sample trays when the tissue sample holder is engaged with the proximal coupler of the probe.

* * * * *